US007928206B2

(12) United States Patent
Knecht et al.

(10) Patent No.: US 7,928,206 B2
(45) Date of Patent: Apr. 19, 2011

(54) PHARMACEUTICAL COMPOSITION COMPRISING A THYMIDINE KINASE POLYNUCLEOTIDE

(76) Inventors: Wolfgang Knecht, Gothenburg (SE); Birgitte Munch-Petersen, Farum (DK); Jure Piskur, Lund (SE)

( * ) Notice: Subject to any disclaimer, the term of this patent is extended or adjusted under 35 U.S.C. 154(b) by 357 days.

(21) Appl. No.: 10/515,417

(22) PCT Filed: May 21, 2003

(86) PCT No.: PCT/DK03/00337
§ 371 (c)(1), (2), (4) Date: Nov. 23, 2004

(87) PCT Pub. No.: WO03/100045
PCT Pub. Date: Dec. 4, 2003

(65) Prior Publication Data

US 2006/0035850 A1 Feb. 16, 2006

(30) Foreign Application Priority Data

May 23, 2002 (DK) ................................ 2002 00794
Feb. 7, 2003 (DK) ................................ 2003 00178

(51) Int. Cl.
*C07H 21/02* (2006.01)
*C12N 9/12* (2006.01)
*C12N 1/20* (2006.01)

(52) U.S. Cl. ..................... 536/23.1; 435/194; 435/252.3

(58) Field of Classification Search ........................ None
See application file for complete search history.

(56) References Cited

U.S. PATENT DOCUMENTS 5,877,010 A 3/1999 Loeb et al.
6,197,743 B1 3/2001 Faller

FOREIGN PATENT DOCUMENTS

WO WO 99/19466 4/1999
WO WO 99/67372 12/1999
WO WO 01/79502 A2 10/2001

OTHER PUBLICATIONS

Munir et al (1993) Proc. Natl. Acad. Sci. USA, vol. 90, p. 4012-4016.*
Boom et al (1990, Journal of Clinical Microbiology, vol. 28, p. 495-503).*
Tris MSDS (Feb. 2002).*
EDTA MSDS (2000).*
Munir et al. (1992) The Journal of Biological Chemistry, vol. 267, p. 6584-6589.*

(Continued)

*Primary Examiner* — Alexander D Kim
(74) *Attorney, Agent, or Firm* — Iver P. Cooper

(57) ABSTRACT

This invention relates to novel plant thymidine kinases and their use in gene therapy. More specifically the invention provides novel thymidine kinases derived from tomato.

In further aspects the invention provides novel polynucleotides encoding the tomato thymidine kinase of mutant thereof, vector constructs comprising the polynucleotide, host cells carrying the polynucleotide or vector, methods of sensitising cells to prodrugs, methods of inhibiting pathogenic agents in warm-blooded animals, methods for biocontrol of plants, methods of synthesizing monophosphates and pharmaceutical compositions comprising the plant thymidine kinases of the invention.

In a preferred embodiment the invention provides a unique combination of a plant thymidine kinase and the nucleoside analog nucleoside analog AZT (3'-azido-3'-deoxythymidine) to treat abnormal cell growth.

44 Claims, 2 Drawing Sheets

OTHER PUBLICATIONS

Sanger et al., (1977) DNA sequencing with chain-terminating inhibitors, vol. 74, p. 5463-5467.*
Oliver et al. (1997) The Journal of Biological Chemistry, vol. 272, pp. 10624-10630.*
Zhang et al., A strategy for rapid cDNA cloning from double-stranded RNA templates isolated from plants infected with RNA viruses by using Taq DNA polymerase., Journal of Virological Methods, 2000, vol. 84, pp. 59-63.*
Strauss et al., Plasmid Expressing the *Herpes simplex* Virus Thymidine Kinase Gene in Mammalian and Bacterial Cells., Mol Gen Genet, 1983, vol. 191, pp. 154-157.*
Wacey et al., Disentangling the perturbational effects of amino acid substitutions in the DNA-binding domain of p53., Hum Genet, 1999, vol. 104, pp. 15-22.*
Kizana et al., Therapeutic Prospects of Cardiac Gene Transfer, Heart, Lung and Circulation, 2007, vol. 16, pp. 180-184.*
Berenstein, Dvora et al., Valine, Not Methionine, Is Amino Acid 106 in Human Cytosolic Thymidine Kinase (TK1), article, 2000, pp. 32187-32192, vol. 275, No. 41, The Journal of Biological Chemistry.
Kokoris, Mark et al., "Characterization of *Herpes simplex* virus type 1 thymidine kinase mutant engineered for improved ganciclovir or acyclovir activity", article, Sep. 2002, pp. 2267-2272, vol. 11, No. 9, Protein Science: A Publication of the Protein Society, United States of America.
Munir , K.M. et al., "Thymidine kinase mutants obtained by random sequence selection.", abstract only, May 1, 1993, 1 page, vol. 11, No. 9, Proceedings of the National Academy of Sciences of the United States of America.
NCBI, Sequence printout for AAF1307, putative thymidine kinase, GI:6466962, PLN Jan. 24, 2001, based on Lin, et al., "*Arabidopsis thaliana* chromosome III P1 MLP3 genomic sequence" [data base accessed Oct. 29, 2004].
NCBI, Sequence printout for AF066050, *Oryza sativa* thymidine kinases, GI:3411151, PLN Jun. 17, 1999, based on Ullah, et al., "A gene for Thymidine Kinase in Plants", Plant Physiol., 119(4):1567, (1999). [data base accessed Apr. 20, 2004].
NCBI, Sequence printout for BAB09824, Contains similarity to thymidine kinase-gene, GI:9759365, PLN Dec. 27, 2000, based on Kotani et al., "Structural analysis of *Arabidopsis thaliana* chromosome", DNA Res. , 4,(4):291-300 (1997) [data base accessed Oct. 29, 2004].
Pantuck, Allan J., et al., "Optimizing Prostate Cancer Suicide Gene Therapy Using *Herpes simplex* Virus Thymidine Kinase Active Site Variants", article, May 1, 2002, pp. 777-789, vol. 13, Human Gene Therapy.
Ullah, Md. Hemayet et al., "A Gene for Thymidine Kinase in Plants", abstract only, 1999, pp. 1567-1568; 1-2, vol. 119, American Society of Plant Physiologists.
Sequence, BE463259, GenBank gi 9509032, NCBI Sequence Viewer Aug. 15, 2005.
Knecht, et al., "Deoxyribonucleoside Kinase Belonging to the Thymidine Kinases 2 (TK2)—like Group Vary significantly in Substrate Specificity, Kinetics and Feed-back Regulation", *J. Mol. Biol.*, vol. 315, pp. 529-540, 2002.
Knecht, et al., "Identification of Residues Involved in the Specificity and Regulation of the Highly Efficient Multisubstrate Deoxyribonucleoside Kinase from *Drosophila melanogaster", J. Mol. Biol.*, vol. 301, pp. 827-837, 2000.
Munch-Petersen, et al., "Functional Expression of a Multisubstrate Deoxyribonucleoside Kinase from *Drosophila melanogaster* and Its C-terminal Deletion Mutants", *The Journal of Biological Chemistry*, vol. 275, No. 9, pp. 6673-6679, Mar. 3, 2000.
Piskur, Jure (Supervisor), "In-Vitro Study of Novel Deoxyribonucleoside Kinases for Gene Therapy", Department of Microbiology, Technical University of Denmark, Cyrille Le Breton Mar.-Aug. 2002.
Sequence, AU068889, GenBank gi 5003740, NCBI Sequence Viewer [Dec. 11, 2004].
Sequence, AW755132, GenBank gi 7676852, NCBI Sequence Viewer [Dec. 11, 2004].
Sequence, BE563259, GenBank gi 9807071, NCBI Sequence Viewer [Dec. 11, 2004].
Sequence, BG129197, GenBank gi 12629385, NCBI Sequence Viewer [Dec. 11, 2004].
Sequence, D24903, GenBank gi 428749, NCBI Sequence Viewer [Dec. 11, 2004].
NCBI, GenBank AF514775, "*Lycopersicon esculentum* TK1-like deoxyribonucleoside kinase mRNA, complete cds", submitted to GenBank by Sandrini, Knecht and Piskur on May 22, 2002, last modified, Jan. 1, 2004.

* cited by examiner

PHARMACEUTICAL COMPOSITION COMPRISING A THYMIDINE KINASE POLYNUCLEOTIDE

TECHNICAL FIELD

This invention relates to novel plant thymidine kinases and their use in gene therapy. More specifically the invention provides novel thymidine kinases derived from tomato, pine, rice or thale cress.

In further aspects the invention provides novel polynucleotides encoding the plant thymidine kinases, vector constructs comprising the polynucleotide, host cells carrying the polynucleotide or vector, methods of sensitising cells to prodrugs, methods of inhibiting pathogenic agents in warm-blooded animals, methods for biocontrol of plants, methods of synthesizing monophosphates and pharmaceutical compositions comprising the plant thymidine kinases of the invention.

In a preferred embodiment the invention provides a unique combination of a plant thymidine kinase and the nucleoside analogue AZT to treat abnormal cell growth.

BACKGROUND ART

DNA is made of four deoxyribonucleoside triphosphates, provided by the de novo and the salvage pathway. The key enzyme of the de novo pathway is ribonucleotide reductase, which catalyses the reduction of the 2'-OH group of the nucleoside diphosphates, and the key salvage enzymes are the deoxyribonucleoside kinases, which phosphorylate deoxyribonucleosides to the corresponding deoxyribonucleoside monophosphates.

Deoxyribonucleoside kinases from various organisms differ in their substrate specificity, regulation of gene expression and cellular localisation. In mammalian cells there are four enzymes with overlapping specificities, the thymidine kinases 1 (TK1) and 2 (TK2), deoxycytidine kinase (dCK) and deoxyguanosine kinase (dGK), which phosphorylate purine and pyrimidine deoxyribonucleosides. TK1 and TK2 are pyrimidine specific and phosphorylate deoxyuridine (dUrd) and thymidine (dThd), and TK2 also phosphorylates deoxycytidine (dCyd). dCK phosphorylates dCyd, deoxyadenosine (dAdo) and deoxyguanosine (dGuo), but not dThd. dGK phosphorylates dGuo and dAdo. TK1 and dCK are cytosolic, and TK2 and dGK are localised in the mitochondria, although recent reports indicate a cytoplasmic localisation of TK2 as well.

Based on homology to a thymidine kinase derived from a Myxoma virus, a gene from rice encoding a thymidine kinase has been proposed [Hemayet Ullah, Dominique Robertson, and Roger C. Fites: A Gene for Thymidine Kinase in Plants (Accession No. AF066050; Plant gene register PGR99-048) *Plant Physiol.* 1999 119 1567]. However, only a partial sequence was isolated, which sequence is not sufficient for expression of the active protein.

Two pieces of genomic DNA from *Arabidopsis thaliana* have been annotated as putative thymidine kinases in GenBank™ (Accession Nos. AAF13097 and BAB09824). However, to this date no experimental work towards characterisation, properties, localisation, use or biological function of plant kinases has yet been accomplished.

AZT (3'-azido-3'-deoxythymidine, Zidovudine, Retrovir®) is a nucleoside analog used in the treatment of HIV-infections. The rate-limiting step of its activation in human cells is the activation of AZT-monophosphate (AZTMP) to AZT-diphosphate.

It has been suggested to use human Herpes simplex virus type 1 thymidine kinase (HSV1-TK), having an endogenous thymidine monophosphate kinase activity, for gene therapy treatment of HIV-infections. HSV1-TK is phylogenetically related to human TK2 but not to human TK1. Also the use of HSV1-TK in order to improve the antiviral activity of zidovudine has been suggested, and the use of HSV1-TK in the combination with AZT has shown to be able to kill transformed *E. coli* bacteria. However, because it is believed that the phoshorylation of AZTMP is the rate limiting step in AZT activation in humans, no experimental work towards an effective combination of AZT and a thymidine kinase for use in the treatment of human cancer or in other human abnormal cell growth related diseases has been accomplished.

SUMMARY OF THE INVENTION

It is an object of the present invention to provide novel plant thymidine kinases useful for converting nucleoside analogs into toxic substances, and useful for converting nucleoside analogues into monophosphates and nucleoside analogue monophosphates into the corresponding diphosphates. The isolated plant thymidine kinases genes can be used in gene therapy for selectively killing cells containing the genes (and being exposed to at least one nucleoside analogue) and the isolated thymidine kinases provided by the present invention can be used for the industrially important process of phosphorylating nucleosides and/or nucleoside analogues. The isolated thymidine kinases can also be used for killing cells by injecting the enzymes into the cells and subjecting the cells to at least one nucleoside analogue. Whenever reference is made to a nucleoside analogue and/or its monophosphate, it is understood that this nucleoside analogue is preferably a deoxynucleoside analogue, more preferably a deoxyribonucleoside analogue, and more preferably AZT.

More specifically the invention provides a unique combination of a plant thymidine kinase and the nucleoside analog AZT to treat abnormal cell growth.

Accordingly, in its first aspect, the invention provides isolated polynucleotides encoding plant thymidine kinase enzymes derived from pine (*Pinus taeda*), from rice (*Oryza sativa*) or from tomato (*Lycopersicum esculentum*). These plant thymidine kinases have turned out to be especially efficient in phosphorylating AZT and possess an unexpected high endogenous monophosphate kinase activity especially on nucleoside analogue monophosphates such as AZTMP.

In another aspect the invention provides isolated polynucleotides encoding thymidine kinase enzymes derived from plants, which thymidine kinase enzymes, when compared to human Herpes simplex virus type 1 thymidine kinase (HSV1-TK) and upon transduction into a eukaryotic or a bacterial cell, decreases at least four (4) fold the $IC_{50}$ of at least one nucleoside analogue. Such low $IC_{50}$ has not been reported for any plant thymidine kinase before. Preferably this nucleoside analogue is AZT.

In a third aspect the invention provides polynucleotides encoding thymidine kinase enzymes derived from plants, which thymidine kinase enzymes are capable of phosphorylating at least one nucleoside analogue monophosphate at higher degree than thymidine monophosphate. Preferably the analogue monophosphate is AZT monophosphate. More preferably said kinases are essentially not capable of phosphorylating thymidine monophosphate. Endogenous monophosphate kinase activity has not been reported for plant thymidine kinases before. Possessing this activity makes the kinases good candidates for medical use such as cancer therapy and for suicide systems. Thus, by having higher substrate specificity for AZT monophosphate than for thymidine monophosphate, AZT monophosphate is converted into the diphosphate at a higher rate.

In a fourth aspect the invention provides polynucleotides encoding thymidine kinase enzymes derived from plants, which thymidine kinase enzymes have a ratio of $[k_{cat}/K_m (Thd)]/[k_{cat}/K_m (AZT)]$ of less than two (2). Thymidine kinases with such a low ratio are relatively more efficient in phosphorylating AZT compared to Thd than known thymidine kinases.

In a fifth aspect the invention provides polynucleotides encoding thymidine kinase enzymes derived from plants, which thymidine kinase enzymes, when expressed and compared to human Herpes simplex virus type 1 thymidine kinase (HSV1-TK), have a decreased ratio of $[k_{cat}/K_m (Thd)]/[k_{cat}/K_m$ (at least one nucleoside analogue)] of at least five (5) fold, wherein the analogue is any nucleoside analogue. Such plant derived thymidine kinases are more effective in the treatment of cancer or other mammalian abnormal cell growth related diseases or in suicide systems than is human Herpes simplex virus type 1 thymidine kinase, which is the most promising enzyme in the prior art for such purpose.

In a sixth aspect the invention provides isolated mutated and/or truncated polynucleotides encoding thymidine kinase enzyme variants derived from plants, which thymidine kinase enzyme variants, when compared to human Herpes simplex virus type 1 thymidine kinase (HSV1-TK) and upon transduction into a eukaryotic or a bacterial cell, decrease at least four (4) fold the $IC_{50}$ of at least one nucleoside analogue. The mutated and/or truncated thymidine kinases have improved substrate specificity for the nucleoside analogues and/or improved stability.

In a seventh aspect the invention provides thymidine kinase enzymes expressed by a polynucleotide of the invention, or thymidine kinase enzyme variants expressed by a mutated (and/or truncated) polynucleotide of the invention.

In an eight aspect the invention provides plant thymidine kinase enzymes derived from thale cress (*Arabidopsis thaliana*), pine (*Pinus taeda*), from tomato (*Lycopersicum esculentum*) or from rice (*Oryza sativa*).

In a ninth aspect the invention provides vector constructs comprising a polynucleotide of the invention, and a promoter operably linked to the polynucleotide.

In a tenth aspect the invention provides packaging cell lines capable of producing infective virions comprising a vector of the invention.

In an eleventh aspect the invention provides host cells comprising a polynucleotide of the invention, or an expression vector of the invention.

In a twelfth aspect the invention provides pharmaceutical compositions comprising a plant thymidine kinase enzyme of the invention, the polynucleotide of the invention, or a packaging cell line of the invention, and a pharmaceutically acceptable carrier or diluent.

In a thirteenth aspect the invention provides methods of sensitising cells to prodrugs, which methods comprise the steps of (i) transfecting or transducing a cell with a polynucleotide sequence encoding a plant thymidine kinase enzyme that promotes the conversion of said prodrug into a (cytotoxic) drug, or otherwise delivering the plant thymidine kinase into the cell; and (ii) delivering a prodrug to said cell; wherein the cell is more sensitive to the (cytotoxic) drug than to the prodrug.

In a fourteenth aspect the invention provides methods of inhibiting pathogenic agents in warm-blooded animals, which methods comprise administering to such animals a polynucleotide of the invention, or a vector of the invention.

In a fifteenth aspect the invention relates to the use of the plant thymidine kinase enzymes of the invention for the phosphorylation of nucleosides or nucleoside analogs.

In a sixteenth aspect the invention provides methods of phosphorylating nucleosides or nucleoside analogs, which methods comprise the steps of (i) subjecting the nucleoside or nucleoside analog to the action of the plant thymidine kinase enzyme of the invention, and (ii) recovering the phosphorylated nucleoside or nucleoside analog.

In a seventeenth aspect the invention relates to a method of controlling or modifying growth of a plant, which plant comprises plant cells comprising a polynucleotide encoding a plant thymidine kinase enzyme of the invention, which method comprises the step of exposing the plant or plant cell to a nucleoside or nucleoside analog.

In a further aspect the invention relates to articles containing a nucleoside analogue and a plant derived thymidine kinase according to the invention or a gene coding for said plant derived thymidine kinase, or a vector comprising said gene coding for said plant derived thymidine kinase, as a combination of the simultaneous, separate or successive administration in cancer therapy.

In a further aspect the invention relates to the medical use of the thymidine kinases of the invention, the genes encoding said thymidine kinases and vectors and host cells expressing said thymidine kinases. Furthermore the invention relates to the use of said enzymes, genes, vectors and cells for the preparation of a medicament for the treatment of a disease related to abnormal cell growth in a human being, preferably the use wherein said disease is cancer.

Other objects of the invention will be apparent to the person skilled in the art from the following detailed description and examples.

DETAILED DISCLOSURE OF THE INVENTION

Plant Thymidine Kinases

In its first aspect the invention provides novel proteins having thymidine kinase (TK) enzyme activity, and which proteins are derived from plants. More specifically the novel plant thymidine kinase enzymes are derived from seed bearing plants (*Spermatophyta*), in particular pine (*Pinus taeda*), tomato (*Lycopersicum esculentum*), rice (*Oryza sativa*), and/or from thale cress (*Arabidopsis thaliana*).

Also it was surprisingly found that two different thymidine kinase enzymes can be isolated from *Arabidopsis thaliana*, herein designated AT-TK1a and AT-TK1b.

In the context of the present invention, a thymidine kinase is an enzyme capable of phosphorylating thymidine but not capable of phosphorylating a purine nucleoside using the assays described in Example 3, Table 5. A thymidine kinase may or may not phosphorylate deoxycytidine.

The thymidine kinase enzymes of the invention are particularly useful for the treatment of abnormal cell growth by activating nucleoside analogs; in particular ATZ.

Based on a Clustal W (1.82) multiple amino acid sequence alignment of the tomato, pine and rice thymidine kinases, three motifs and several conserved, semi-conserved and lesser-conserved residues were identified, as shown in Table 1 below. In Table 1, alignment starts with amino acid residue no. 65 of the Rice TK1, because the first 64 amino acids do not align to the other thymidine kinases.

TABLE 1

CLUSTAL W (1.82) Multiple Amino Acid Sequence Alignment

```
Rice-TK1   ---------- ---------- ---------- ---------- -MEAQPSYP- ----------   (008)
Tomato-TK1 ---------- ---------- ---------- ---------- -MAFSSSARN PVDLRNGSKN   (019)
AT-TK1a    ---------- ---------- ---------- ---------- -MATLKASFL IKTLDSDVTG   (019)
Pine-TK1   ---------- ---------- ---------- ---------- -MDDSGIYT- ----------   (008)
AT-TK1b    MRTLISPSLA PFSLHLHKPS LFSTALRFSF SIINITPTNS PPSTISTRKL QTKATRVTSS   (060)

Rice-TK1   ---------- -GEIHVIVGP MFAGKTTALL RRVQVEAGTG RNVALIKSDK DNRYGLDSVV   (057)
Tomato-TK1 SFC------P VGEIHVIVGP MFAGKTTALL RRVNLESNDG RNVVLIKSSK DARYAVDAVV   (073)
AT-TK1a    DFLSDLEPRG SGAVHVIMGP MFSGKSTSLL RRIKSEISDG RSVAMLKSSK DTRYAKDSVV   (079)
Pine-TK1   ---------- SGEIHLILGP MFAGKTTALI RKMRAEIQMG RRVVLVKSDK DTRYGLNSVV   (058)
AT-TK1b    SSSQPLSSSS PGEIHVVVGP MFSGKTTTLL RRILAERETG KRIAIIKSNK DTRYCTESIV   (120)
                       * :*:::** **:**:*:*: *::  *   * : :.::**.* * **  :::*

Rice-TK1   THDGTKMPCW ALPELSSFQD KLGTEAYD-K VDVIGIDEAQ FFDDLHDFCC KAADRDGKIV   (116)
Tomato-TK1 THDGTRFPCW SLPDLSSFKQ RFGEDAYE-K VDVIGIDEAQ FFGDLYEFCC NAADFDGKII   (132)
AT-TK1a    THDGIGFPCW ALPDLMSFPE KFGLDAYN-K LDVIGIDEAQ FFGDLYEFCC KVADDDGKIV   (138)
Pine-TL1   SHDGAKMPCW AVADLASFKG KLGEEAYK-Q VDVIGIDEAQ FFKDLYSFCQ VAADRDGKIV   (117)
AT-TK1b    THDGEKYPCW SLPDLSSFKE EPGFDDYENR LDVIGIDEAQ FFGDLYEFCR EAADKEGKTV   (180)
           :***   *** ::.:* **   ::* : *. : :********* ** **:.**   .** :** :
                                              -------- --
                                                Motif I

Rice-TK1   VVAGLDGDYK RNKFGSVLDI IPLADSVTKL TARCELCGRR AFFTLRKTRE TKTELIGGAD   (176)
Tomato-TK1 VVAGLDGDYL RKSFGSVLDI IPLADTVTKL TARCELCNRR AFFTFRKTNE TETELIGGAD   (192)
AT-TK1a    IVAGLDGDYL RRSFGAVLDI IPIADSVTKL TARCEVCGHK AFFTLRKNCD TRTELIGGAD   (198)
Pine-TK1   IVAGLDGDYL RKSFGSALEL IPIADSVVKL KSRCELCGKA ASFTFRKTGE RKTEVVGGAD   (177)
AT-TK1b    IVAGLDGDFM RRRFGSVLDL IPIADTVTKL TSRCEVCGKR ALFTMRKTEE KETELIGGAE   (240)
           :*******:  *. **:.*:: **:**:*.** .:***:*.:  * **:**. :   .**::***:
           ------C                      ---- ------
           Motif II                  Lid region

Rice-TK1   VYMPVCRQHY LDGQIVIEAT RIVLD-LEKS KVIHAFK--- ---                    (212)
           (amino acids 65-277 of SEQ ID NO: 7)
Tomato-TK1 IYMPVCRQHY VNGQSVNESA KMVLE-SHKV SNELILESPL VDP (SEQ ID NO: 4)     (234)
AT-TK1a    VYMPVCRKHY ITNHIVIKAS KKVLEDSDKA RAESCVAATI --- (SEQ ID NO: 9)     (238)
Pine-TK1   VYMPVCRRHY VNGQIVIDTT EAVLE-SPEV QYDACAQATT TSG (SEQ ID NO: 2)     (219)
AT-TK1b    VYMPVCRSHY VCGQNVLETA RAVLD---SS NNHSVVASSL --- (SEQ ID NO: 13)    (277)
           :****** ** : .: * .:: : **:   .
           ------
           Motif III
```

- designates motifs (Motif I, Motif II and Motif III)
* designates conserved residues
: designates semi-conserved residues
. designates lesser-conserved residues Therefore, in a preferred embodiment the plant thymidine kinase enzyme of the invention comprises one or more of the following three motifs:

```
Val Ile Gly Ile Asp Glu Ala Gln Phe Phe (Motif I)
(amino acids 105-114 of SEQ ID NO: 4)

Val Ala Gly Leu Asp Gly                 (Motif II)
(amino acids 134-139 of SEQ ID NO: 4)

Tyr Met Pro Val Cys Arg                 (Motif III)
(amino acids 194-199 of SEQ ID NO: 4)
```

In another preferred embodiment, the plant thymidine kinase enzyme of the invention comprises the Lid region:

Val A1 Lys Leu A2 A3 Arg Cys Glu A4 (Lid region) (SEQ ID NO:37), wherein A1 is selected from Thr and Val, A2 is selected from Thr and Lys, A3 is selected from Ala and Ser, and A4 is selected from Leu and Val.

In a more preferred embodiment the plant thymidine kinase enzyme of the invention comprises all of the conserved residues identified in Table 1.

Identity of Polypeptides

In another preferred embodiment the plant thymidine kinase enzyme of the invention comprises the amino acid sequence presented as SEQ ID NO: 2, as SEQ ID NO: 4, as SEQ ID NO: 5, as SEQ ID NO: 7, as SEQ ID NO: 9, as SEQ ID NO: 11, or as SEQ ID NO: 13, or an amino acid sequence that has at least 30%, preferably at least 50%, more preferred at least 70%, even more preferred at least 80%, still more preferred at least 90%, yet more preferred at least 95% identity, most preferred at least 98% identity, when determined over the entire length of the SEQ ID.

In the context of this invention "identity" is a measure of the degree of homology of amino acid sequences. In order to characterize the identity, subject sequences are aligned so that the highest order homology (match) is obtained. Based on these general principles the "percent identity" of two amino acid sequences is determined using the BLASTP algorithm [Tatiana A. Tatusova, Thomas L. Madden: Blast 2 sequences—a new tool for comparing protein and nucleotide sequences; *FEMS Microbiol. Lett.* 1999 174 247-250], which is available from the National Center for Biotechnology Information (NCBI) web site, and using the default settings suggested here (i.e. Matrix=Blosum62; Open gap=11; Extension gap=1; Penalties gab x_dropoff=50; Expect=10; Word size=3; Filter on). The BLAST algorithm determines the % sequence identity in a range of overlap between two aligned sequences. For the purposes of the present invention, the percent sequence identity is calculated in a range of overlap of at least 50 amino acids, more preferably at least 75 amino acids, more preferably at least 100 amino acids, the range being calculated by BLASTP under default settings.

The results of this BLASTP comparison are presented in Table 2.

TABLE 2

BLASTP Comparison of Protein Sequences of Thymidine Kinases of Different Plant Origin

| TK | Tomato | Rice | AT(a) | AT(b) |
|---|---|---|---|---|
| Pine | 65/82/197 | 69/84/193 | 59/77/208 | 62/83/195 |
| Tomato | — | 75/86/196 | 69/84/193 | 65/81/208 |
| Rice | — | — | 69/84/193 | 65/83/197 |
| AT(a) | — | — | — | 60/78/215 |

Identities (%)/Positives (%)/length of the compared fragment
Pine (*Pinus taeda*) thymidine kinase
Tomato (*Lycopersicum esculentum*) thymidine kinase
Rice (*Oryza sativa*) thymidine kinase
Thale cress (*Arabidopsis thaliana*) thymidine kinases (a) and (b)

In a preferred embodiment the plant thymidine kinase enzyme of the invention is derived from pine, and has at least at least 60%, preferably at least 70%, more preferred at least 80%, even more preferred at least 90%, yet more preferred at least 95%, most preferred at least 98% sequence identity to the sequence presented in SEQ ID NO: 2.

In another preferred embodiment the plant thymidine kinase enzyme of the invention is derived from tomato, and has at least at least 60%, preferably at least 70%, more preferred at least 80%, even more preferred at least 90%, yet more preferred at least 95%, most preferred at least 98% sequence identity to any of the sequences SEQ ID NO: 4 or 5.

In a third preferred embodiment the plant thymidine kinase enzyme of the invention is derived from rice, and has at least at least 60%, preferably at least 70%, more preferred at least 80%, even more preferred at least 90%, yet more preferred at least 95%, most preferred at least 98% sequence identity to the sequence SEQ ID NO: 7.

In a fourth preferred embodiment the plant thymidine kinase enzyme of the invention is derived from *Arabidopsis thaliana*, and has at least at least 60%, preferably at least 70%, more preferred at least 80%, even more preferred at least 90%, yet more preferred at least 95%, most preferred at least 98% sequence identity to the sequence SEQ ID NO:9 or 11.

In a fifth embodiment the plant thymidine kinase enzyme of the invention is also derived from *Arabidopsis thaliana*, and has at least at least 60%, preferably at least 70%, more preferred at least 80%, even more preferred at least 90%, yet more preferred at least 95%, most preferred at least 98% sequence identity to the sequence SEQ ID NO: 13.

Variant Polypeptides

In a most preferred embodiment the plant thymidine kinase enzyme of the invention comprises the amino acid sequence presented as SEQ ID NO: 2, as SEQ ID NO: 4, as SEQ ID NO: 5, as SEQ ID NO: 7, as SEQ ID NO: 9, as SEQ ID NO: 11, or as SEQ ID NO: 13, or a functional analogue thereof.

In the context of this invention, the term "functional analog" means a polypeptide (or protein) having thymidine kinase activity and having an amino acid sequence that differs from the sequence presented as SEQ ID NO: 2, as SEQ ID NO: 4, as SEQ ID NO: 5, as SEQ ID NO: 7, as SEQ ID NO: 9, as SEQ ID NO: 11, or as SEQ ID NO: 13, at one or more amino acid positions. Such analogous polypeptides include polypeptides comprising conservative substitutions, splice variants, isoforms, homologues from other species, and polymorphisms.

As defined herein, the term "conservative substitutions" denotes the replacement of an amino acid residue by another, biologically similar residue. Examples of conservative substitutions include (i) the substitution of one non-polar or hydrophobic residue such as alanine, leucine, isoleucine, valine, proline, methionine, phenylalanine or tryptophan for another, in particular the substitution of alanine, leucine, isoleucine, valine or proline for another, or
(ii) the substitution of one neutral (uncharged) polar residue such as serine, threonine, tyrosine, asparagine, glutamine, or cysteine for another, in particular the substitution of arginine for lysine, glutamic for aspartic acid, or glutamine for asparagine; or
(iii) the substitution of a positively charged residue such as lysine, arginine or histidine for another, or
(iv) the substitution of a negatively charged residue such as aspartic acid or glutamic acid for another.

The term conservative substitution also include the use of a substituted amino acid residue in place of a parent amino acid residue, provided that antibodies raised to the substituted polypeptide also immunoreact with the un-substituted polypeptide.

Modifications of this primary amino acid sequence may result in proteins which have substantially equivalent activity as compared to the unmodified counterpart polypeptide, and thus may be considered functional analogous of the parent proteins. Such modifications may be deliberate, e.g. as by site-directed mutagenesis, or they may occur spontaneous, and include splice variants, isoforms, homologues from other species, and polymorphisms. Such functional analogous are also contemplated according to the invention.

C-terminal Deletions

In another embodiment the invention provides plant thymidine kinase enzymes having C-terminal deletions when compared to the parent (wild-type) enzyme. Such truncated enzymes may be obtained by conventional techniques, e.g. site-directed mutagenesis, or as described in the working examples.

According to the invention it has been found that C-terminal deletions create enzymes of improved properties, in particular increased stability, and/or improved substrate specificity, when compared to the wild-type enzyme.

In a more preferred embodiment the invention provides thymidine kinase enzymes having a C-terminal deletion in the order of 1-60 amino acid residues, preferably 1-50 amino acid residues, more preferred 1-40 amino acid residues, even more preferred 1-30 amino acid residues, yet more preferred 1-26 amino acid residues, most preferred 1-24 amino acid residues.

In an even more preferred embodiment, the plant thymidine kinase enzyme of the invention is a thymidine kinase enzyme derived from tomato that has a C-terminal deletion of 26 amino acid residues. In a most preferred embodiment the plant thymidine kinase enzyme of the invention is a thymidine kinase enzyme having the amino acid sequence of SEQ ID NO: 5.

In a yet more preferred embodiment, the plant thymidine kinase enzyme of the invention is a thymidine kinase enzyme derived from *Arabidopsis thaliana* that has a C-terminal deletion of 24 amino acid residues. In a most preferred embodiment the plant thymidine kinase enzyme of the invention is a thymidine kinase enzyme having the amino acid sequence of SEQ ID NO: 11.

N-Terminal Deletions

N-terminal deletions are also contemplated, in particular the deletion of the N-terminal 22 amino acids and the deletion of the N-terminal 45 amino acids or of the N-terminal 63 amino acids of the AT-TK1b (SEQ ID NO: 13). These amino acids constitute a putative organelle signal peptide. As evidenced by Example 4 (Table 8) deletion of these N-terminal amino acids decreases the $LD_{100}$ for AZT significantly.

Polynucleotides Encoding Plant Thymidine Kinases

In another aspect the invention provides isolated polynucleotides encoding plant thymidine kinase enzymes derived from pine, tomato, rice or thale cress, preferably those plant thymidine kinase enzymes described above.

Hybridisation Protocol

In a preferred embodiment, the isolated polynucleotide of the invention is capable of hybridising with the polynucleotide sequence presented as SEQ ID NO: 1, as SEQ ID NO: 3, as SEQ ID NO: 6, as SEQ ID NO: 8, as SEQ ID NO: 10, as SEQ ID NO: 12, or its complementary strand.

Hybridization should be accomplished under at least low stringency conditions, but preferably at medium or high stringency conditions.

Suitable experimental conditions for determining hybridisation at low, medium, or high stringency conditions, respectively, between a nucleotide probe and a homologous DNA or RNA sequence, involves pre-soaking of the filter containing the DNA fragments or RNA to hybridise in 5×SSC [Sodium chloride/Sodium citrate; cf. Sambrook et al.; *Molecular Cloning: A Laboratory Manual*, 2nd Ed., Cold Spring Harbor Lab., Cold Spring Harbor, N.Y. 1989] for 10 minutes, and prehybridization of the filter in a solution of 5×SSC, 5×Denhardt's solution [cf. Sambrook et al.; Op cit.], 0.5% SDS and 100 μg/ml of denatured sonicated salmon sperm DNA [cf. Sambrook et al.; Op cit.], followed by hybridisation in the same solution containing a concentration of 10 ng/ml of a random-primed [Feinberg A P & Vogelstein B; *Anal. Biochem.* 1983 132 6-13], $^{32}$P-dCTP-labeled (specific activity>$1\times10^9$ cpm/μg) probe for 12 hours at approximately 45° C.

The filter is then washed twice for 30 minutes in 2×SSC, 0.5% SDS at a temperature of at least 55° C. (low stringency conditions), more preferred of at least 60° C. (medium stringency conditions), still more preferred of at least 65° C. (medium/high stringency conditions), even more preferred of at least 70° C. (high stringency conditions), and yet more preferred of at least 75° C. (very high stringency conditions).

The complementary nucleic acids or signal nucleic acids may be labelled by conventional methods known in the art to detect the presence of hybridised oligonucleotides. The most common method of detection is the use of autoradiography with e.g. $^{3}$H, $^{125}$I, $^{35}$S, $^{14}$C, or $^{32}$P-labelled probes, which may then be detected using an X-ray film. Other labels include ligands, which bind to labelled antibodies, fluorophores, chemoluminescent agents, enzymes, or antibodies, which can then serve as specific binding pair members for a labelled ligand.

Identity of DNA Sequences

In another preferred embodiment, the isolated polynucleotide of the invention has at least 73%, preferably at least 75%, more preferred at least 80%, even more preferred at least 90%, yet more preferred at least 95%, most preferred at least 98% identity to the polynucleotide sequence presented as SEQ ID NO: 1, as SEQ ID NO: 3, as SEQ ID NO: 6, as SEQ ID NO: 8, as SEQ ID NO: 10, or as SEQ ID NO: 12, when determined over the entire length of the SEQ ID NO:. For the purposes of the present invention the percent sequence identity is calculated when BLASTN provides a range of overlap of at least 100 nucleotides, the range being determined under default settings. More preferably the range of overlap is at least 150 nucleotides, more preferably at least 225 nucleotides, more preferably at least 300 nucleotides.

In the context of this invention, "identity" is a measure of the degree of homology of nucleotide sequences. In order to characterize the identity, subject sequences are aligned so that the highest order homology (match) is obtained. Based on these general principles, the "percent identity" of two amino acid sequences or of two nucleic acids is determined using the BLASTN algorithm [Tatiana A. Tatusova, Thomas L. Madden: Blast 2 sequences—a new tool for comparing protein and nucleotide sequences; *FEMS Microbiol. Lett.* 1999 174 247-250], which is available from the National Center for Biotechnology Information (NCBI) web site, and using the default settings suggested here (i.e. Reward for a match=1; Penalty for a match=−2; Strand option=both strands; Open gap=5; Extension gap=2; Penalties bap x_dropoff=50; Expect=10; Word size=11; Filter on). The BLASTN algorithm determines the % sequence identity in a range of overlap between two aligned nucleotide sequences. For the purposes of the present invention the percent sequence identity is calculated in a range of overlap of at least 100 nucleotides, the range being determined by BLASTN under default settings. More preferably the range of overlap is at least 300 nucleotides.

The results of this BLASTN comparison are presented in Table 3.

TABLE 3

BLASTN Comparison of Nucleotide Sequences of Thymidine Kinases of Different Plant Origin

| TK | Tomato | Rice | AT(a) | AT(b) |
|---|---|---|---|---|
| Pine | 74/194* 82/51 | 76/158 | 72/236 | 74/206 |
| Tomato | — | 73/383 | 74/503 | 74/285 |
| Rice | — | — | 74/315 | ◇ |
| AT(a) | — | — | — | 77/200 |

Identities (%)/length of the compared fragment
*divided into an N-and a C-terminal fragment
◇ No significant similarity
Pine (*Pinus taeda*) thymidine kinase
Tomato (*Lycopersicum esculentum*) thymidine kinase
Rice (*Oryza sativa*) thymidine kinase
*Arabidopsis thaliana* thymidine kinase (a) and (b)

Analogous DNA Sequences

In its most preferred embodiment, the isolated polynucleotide of the invention comprises the polynucleotide sequence presented as SEQ ID NO: 1, as SEQ ID NO: 3, as SEQ ID NO: 6, as SEQ ID NO: 8, as SEQ ID NO: 10, or as SEQ ID NO: 12, or a functional analog thereof.

In the context of this invention, the term "functional analog" covers conservatively modified polynucleotides, and polynucleotides encoding functionally equivalent polypeptides.

In the context of this invention, the term "conservatively modified polynucleotides" refers to those nucleic acids which encode identical or essentially identical amino acid sequences, or where the nucleic acid does not encode an amino acid sequence, to essentially identical sequences.

Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein, which encodes a polypeptide, also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid, which encodes a polypeptide, is implicit in each described sequence.

Expression Vectors

In a third aspect the invention provides recombinant expression vectors comprising the isolated polynucleotide of the invention and a promoter operably linked to the polynucleotide.

The expression vector of the invention preferably is one suitable for carrying out expression in a eukaryotic organism.

In a more preferred embodiment the expression vector of the invention is a viral vector, in particular a Herpes simplex viral vector, an adenoviral vector, an adenovirus-associated viral vector, a lentivirus vector, a retroviral vector or a vacciniaviral vector.

Packaging Cell Lines

In a fourth aspect the invention provides packaging cell lines capable of producing an infective virion, which cell line comprises a vector of the invention.

Packaging cells refers to cells containing those elements necessary for production of infectious recombinant vira, which are lacking in a recombinant virus vector. Methods for preparation of packaging cell lines are known in the prior art.

Host Cells

In a fifth aspect the invention provides an isolated host cell comprising the isolated polynucleotide of the invention, or the expression vector of the invention.

In a preferred embodiment the host cell of the invention is an a bacterial cell, preferably a eukaryotic cell, in particular a mammalian cell, a human cell, an oocyte, or a yeast cell.

In a more preferred embodiment the host cell of the invention is a human cell, a dog cell, a monkey cell, a rat cell, a pig cell, or a mouse cell.

Pharmaceutical Compositions

In a sixth aspect the invention relates to novel pharmaceutical compositions comprising a therapeutically effective amount of the plant thymidine kinase enzyme of the invention, or the host cell of the invention, and a pharmaceutically acceptable carrier or diluent.

For use in therapy the plant thymidine kinase enzyme of the invention may be administered in any convenient form. In a preferred embodiment, plant thymidine kinase enzyme of the invention is incorporated into a pharmaceutical composition together with one or more adjuvants, excipients, carriers and/or diluents, and the pharmaceutical composition prepared by the skilled person using conventional methods known in the art.

Such pharmaceutical compositions may comprise plant thymidine kinase enzyme of the invention, or antibodies against a plant thymidine kinase. The composition may be administered alone or in combination with one or more other agents, drugs or hormones.

The pharmaceutical composition of this invention may be administered by any suitable route, including, but not limited to oral, intravenous, intramuscular, interarterial, intramedullary, intrathecal, intraventricular, transdermal, subcutaneous, intraperitoneal, intranasal, anteral, topical, sublingual or rectal application, buccal, vaginal, intraorbital, intracerebral, intracranial, intraspinal, intraventricular, intracisternal, intracapsular, intrapulmonary, transmucosal, or via inhalation.

Further details on techniques for formulation and administration may be found in the latest edition of *Remington's Pharmaceutical Sciences* (Maack Publishing Co., Easton, Pa.).

The active ingredient may be administered in one or several doses per day. Currently contemplated appropriate dosages are between 0.5 ng to about 50 μg/kg thymidine kinase/kg body weight per administration, and from about 1.0 ng/kg to about 100 μg/kg daily.

The dose administered must of course be carefully adjusted to the age, weight and condition of the individual being treated, as well as the route of administration, dosage form and regimen, and the result desired, and the exact dosage should of course be determined by the practitioner.

In further embodiments, the plant thymidine kinase of the invention may be administered by genetic delivery, using cell lines and vectors as described below under methods of treatment.

Therefore, in another preferred embodiment, the invention provides pharmaceutical compositions comprising the polynucleotide of the invention, or a vector of the invention, or a packaging cell of the invention, or a host cell of the invention, and a pharmaceutically acceptable carrier or diluent.

To generate such therapeutic cell lines, the polynucleotide of the invention may be inserted into an expression vector, e.g. a plasmid, virus or other expression vehicle, and operatively linked to expression control sequences by ligation in a way that expression of the coding sequence is achieved under conditions compatible with the expression control sequences.

Suitable expression control sequences include promoters, enhancers, transcription terminators, start codons, splicing signals for introns, and stop codons, all maintained in the correct reading frame of the polynucleotide of the invention so as to permit proper translation of mRNA. Expression control sequences may also include additional components such as leader sequences and fusion partner sequences.

Methods of Treatment

The present invention, which relates to polynucleotides and proteins, polypeptides, peptide fragments or derivatives produced therefrom, as well as to antibodies directed against such proteins, peptides or derivatives, may be used for treating or alleviating a disorder or disease of a living animal body, including a human, which disorder or disease is responsive to the activity of a cytotoxic agent.

The disorder, disease or condition may in particular be a cancer or a viral infection.

Cancer cells are rapidly proliferating cells with the ability to invade and metastatize adjacent tissue and hence compromise the function of essential body parts leading to severe illness and death. The usual treatments are surgery, radiation and chemotherapy, and recently a novel treatment, genetherapy, has emerged. In gene directed enzyme prodrug therapy (GDEPT) a gene is delivered to the cancer cells, and expressed there. The corresponding enzyme later converts the administered prodrug to an active form, arresting cell proliferation. One of the GDEPT systems is based on deoxyribonucleoside kinases and different prodrugs, nucleoside analogues.

The polynucleotides of the present invention may in particular be used as a "suicide gene", i.e. a drug-susceptibility gene. Transfer of a suicide gene to a target cell renders the cell sensitive to compounds or compositions that are relatively non-toxic to normal cells.

Therefore, in a seventh aspect, the invention provides a method for sensitising target cells to prodrugs, which method comprises the steps of (i) transfecting or transducing the target cell with a polynucleotide sequence encoding a plant thymidine kinase enzyme that promotes the conversion of said prodrug into a (cytotoxic) drug, or otherwise delivering the plant thymidine kinase into the cell; and (ii) delivering said prodrug to said target cell;

wherein said target cell is more sensitive to said (cytotoxic) drug than to said prodrug.

The target cell may be any cell of interest, in particular a human cell, a dog cell, a monkey cell, a rat cell, a cat cell, a pig cell, or a mouse cell. Preferably the target cell is a human cell.

In its broadest aspect any plant thymidine kinase enzyme may be used. However, in a preferred embodiment, the polynucleotide sequence encoding a plant thymidine kinase enzyme is a polynucleotide sequence of the invention.

In a more preferred embodiment the prodrug is a nucleoside analogue.

In the context of this invention a preferred nucleoside analogue for use according to the invention is selected from the group consisting of aciclovir (9-[2-hydroxy-ethoxy]-methyl-guanosine), buciclovir (9-(3,4-dihydroxybutyl)guanine), famciclovir (2-[2-(2-Amino-9H-purin-9-yl) ethyl]-1,3-propanediol diacetate), ganciclovir (9-[2-hydroxy-1-(hydroxymethyl)ethoxyl-methyl]-guanosine), penciclovir, valciclovir, trifluorothymidine, AZT (3'-azido-3'-deoxythymidine), AIU (5'-iodo-5'-amino-2',5'-dideoxyuridine), ara-A (adenosine-arabinoside; Vivarabine), ara-C (cytidine-arabinoside), ara-G (9-beta-D-arabinofuranosylguanine), ara-T, 1-beta-D-arabinofuranosyl thymine, 5-ethyl-2'-deoxyuridine, 5-iodo-5'-amino-2,5'-dideoxyuridine, 1-[2-deoxy-2-fluoro-beta-D-arabino furanosyl]-5-iodouracil, idoxuridine (5-iodo-2'deoxyuridine), fludarabine (2-Fluoroadenine 9-beta-D-Arabinofuranoside), gencitabine, 3'-deoxyadenosine (3-dA), 2',3'-dideoxyinosine (ddI), 2',3'-dideoxycytidine (ddC), 2',3'-dideoxythymidine (ddT), 2',3'-dideoxyadenosine (ddA), 2',3'-dideoxyguanosine (ddG), 2-chloro-2'-deoxyadenosine (2CdA), 5-fluorodeoxyuridine, BVaraU ((E)-5-(2-bromovinyl)-1-beta-D-arabinofuranosyluracil), BVDU (5-bromovinyl-deoxyuridine), FIAU (1-(2'-deoxy-2'-fluoro-beta-D-arabinofuranosyl)-5-iodouracil), 3TC (2'-deoxy-3'-thiacytidine), dFdC gemcitabine (2',2'-difluorodeoxycytidine), dFdG (2',2'-difluorodeoxyguanosine), 5-fluorodeoxyuridine (FdUrd), d4T (2',3'didehydro-3'-deoxythymidine), ara-M (6-methoxy purinearabinonucleoside), ludR (5-Jodo-2' deoxyuridine), CaFdA (2'-chloro-2'-ara-fluoro-deoxyadenosine), ara-U (1-beta-D-arabinofuranosyluracil), FBVAU (E)-5-(2'-bromovinyl)-1-(2-deoxy-2-fluoro-beta-D-arabinofuranosyl)uracil, FMAU 1-(2-deoxy-2-fluoro-beta-D-arabinofuranosyl)-5-methyluracil, FLT 3'-fluoro-2'-deoxythymidine, 5-Br-dUrd 5-bromodeoxyuridine, 5-Cl-dUrd 5-chlorodeoxyuridine or dFdU 2',2'-difluorodeoxyuridine.

In a more preferred embodiment the nucleoside analog for use according to the invention is AZT (3'-azido-3'-deoxythymidine).

The thymidine kinase enzyme invention may be used directly via e.g., injected, implanted or ingested pharmaceutical compositions to treat a pathological process responsive to the thymidine kinase enzyme.

The polynucleotide of the invention, including the complementary sequences thereof, may be used for the expression of the thymidine kinase enzyme of the invention. This may be achieved by cell lines expressing such proteins, peptides or derivatives of the invention, or by virus vectors encoding such proteins, peptides or derivatives of the invention, or by host cells expressing such proteins, peptides or derivatives. These cells, vectors and compositions may be administered to treatment of target areas to affect a disease process responsive to cytotoxic agents.

Suitable expression vectors may be a viral vector derived from Herpes simplex, adenovira, lentivira, retrovira, or vaccinia vira, or from various bacterially produced plasmids, and may be used for in vivo delivery of nucleotide sequences to a whole organism or a target organ, tissue or cell population. Other methods include, but are not limited to, liposome transfection, electroporation, transfection with carrier peptides containing nuclear or other localising signals, and gene delivery via slow-release systems. Specific cells may be targeted by using cell surface markers, such as markers specific for cancer cells. Both the protein and a vector construct can be targeted to cells using cell surface markers. Dividing cells may be targeted by transducing with a retroviral vector, which only infects dividing cells.

In still another aspect of the invention, "antisense" nucleotide sequences complementary to the nucleotide of the invention or portions thereof, may be used to inhibit or enhance thymidine kinase enzyme expression.

In another preferred embodiment the invention provides methods for inhibiting pathogenic agents in warm-blooded animals, which methods comprises the step of administering to said animal a polynucleotide of the invention, or an expression vector of the invention.

In a more preferred embodiment the polynucleotide sequence or the expression vector is administered in vivo.

In another preferred embodiment the pathogenic agent is a virus, a bacterium or a parasite, or even a tumour cell.

In another preferred embodiment the pathogenic agent is an autoreactive immune cell.

In an even more preferred embodiment the method further comprises the step of administering a nucleoside analogue to said warm-blooded animal.

Preferably the nucleoside analogue is selected from those described above.

In a most preferred embodiment the nucleoside analog for use according to the invention is AZT (3'-azido-3'-deoxythymidine).

Suicide Systems

One very important use of the thymidine kinase encoding genes of the present invention is for suicide systems in cell and gene based therapy. In all types of cell and gene therapy on mammals there is a need to have systems which enable the irreversible killing of transplanted cells or cells which have been transduced by the gene therapy.

There are basically two types of cell based therapies which both can benefit from having a built-in suicide system based on the thymidine kinases according to the present invention. In replacement cell therapy, naked cells are transplanted into a subject to replace cells that have lost the ability to fulfil their function in the body or to replace dead cells. Once these cells have been transplanted and are fully integrated into the body of the subject they cannot easily be removed by surgical means. By having a built-in suicide system in which a thymidine kinase of the present invention is expressed constitutively or inducibly, the cells can be killed by administering to the individual a therapeutically effective amount of a nucleoside analog, such as AZT. The nucleoside analogue can be administered if the transplanted cells start to proliferate in an uncontrolled manner. One may also wish to terminate the treatment simply because there is no need for the replacement cells anymore or because further treatment is by some other route.

The other type of cell-based therapy includes therapeutic cells which are transplanted into the body to secrete e.g. a growth factor in a certain location. Often such therapeutic cells are encapsulated and can relatively easily be removed from the body again but the incorporation of a suicide system is preferred because the cells can be killed selectively without the use of surgery.

In in vivo gene therapy the same considerations apply as with replacement cell therapy. The incorporation of a suicide gene can be achieved by construction a viral vector comprising both the therapeutic gene and a thymidine kinase according to the present invention. Preferably the therapeutic gene and the thymidine kinase is inserted under the control of the same promoter, optionally by separating them with an IRES construct.

In the cases where transplanted cells have been conditionally immortalised before transplantation there is a theoretical risk that the oncogene initiates transcription after transplantation and that the transplanted cells consequently become tumorigenic. Means to control this situation are made available by the present invention. Whenever cells are immortalised by transduction with an oncogene under the control of an inducible promoter (e.g. the Tet on-off system, the Mx1 promoter or the like), a thymidine kinase is inserted into the vector construct under the control of the same promoter (or using an IRES construct). This ensures that whenever the oncogene is transcribed, the thymidine kinase is also transcribed and the transduced and tumorigenic cells can be selectively killed by administering a nucleoside analogue, such as AZT.

Method of Phosphorylating Nucleosides

The thymidine kinase enzyme of the invention may find different utility, including both therapeutic and biotechnological applications.

In an eight aspect the invention relates to use of the plant thymidine kinase enzyme of the invention for phosphorylating nucleosides or a nucleoside analogs.

In a preferred embodiment the invention provides a method for phosphorylating a nucleoside or a nucleoside analog, comprising the steps of i) subjecting the nucleoside or nucleoside analog to the action of the plant thymidine kinase enzyme of the invention; and
ii) recovering the phosphorylated nucleoside or nucleoside analog.

In particular, the thymidine kinases of the present invention may be used for phosphorylating dideoxyguanosine.

Genetically Modified Plants

The thymidine kinase enzyme of the invention may also find utility in methods for modifying or controlling plant growth. Therefore, in a further aspect, the invention relates to a method of controlling or modifying growth of a plant, which plant comprises plant cells comprising a polynucleotide encoding a plant thymidine kinase enzyme of the invention, which method comprises the step of exposing the plant or plant cell to a nucleoside or nucleoside analog, preferably AZT. By the discovery of hitherto unknown properties of plant thymidine kinases and in particular those described in the present invention, the inventors contemplate the use of nucleoside analogues as herbicides. As plant thymidine kinases convert nucleoside analogues at a very high rate into toxic substances, nucleoside analogues can be used as herbicides for plants having these thymidine kinases either by nature or as a heterologous gene. By inserting the thymidine kinases of the present invention into plants not having a thymidine kinase with these properties, the plant is rendered susceptible to nucleoside analogs in particular susceptible to AZT.

The polynucleotide encoding plant thymidine kinase enzyme of the invention preferably is a heterologous polynucleotide, and the plant subjected to the method of the invention preferably is a transgenic plant.

Therefore, in a yet further aspect, the invention provides transgenic plants comprising an expressible heterologous nucleic acid encoding the plant thymidine kinase enzyme of the invention, wherein the heterologous nucleic acid is introduced into the transgenic plant, or an ancestor of the transgenic plant.

The transgenic plant may be obtained by known techniques for producing genetically modified plants, e.g. by introducing into a plant cell an expression vector of the invention.

Any plant thymidine kinase may also be knocked out and/or functionally replaced by other thymidine kinase, said other kinase not being able to convert a certain nucleoside analog (for example in crop plants). The nucleoside analogue may then be used to kill weed around this genetically modified plant.

Any transformed plant obtained according to the invention can be used in a conventional breeding scheme or in vitro plant propagation to produce more transformed plants with the same characteristics and/or can be used to introduce the same characteristics in other varieties of the same or related species. Such plants are also part of the invention. Seeds obtained from the transformed plants contain the same genetical characteristics and also form part of the invention.

BRIEF DESCRIPTION OF THE DRAWINGS

The present invention is further illustrated by reference to the accompanying drawing, in which.

EXAMPLES

Figure 1:
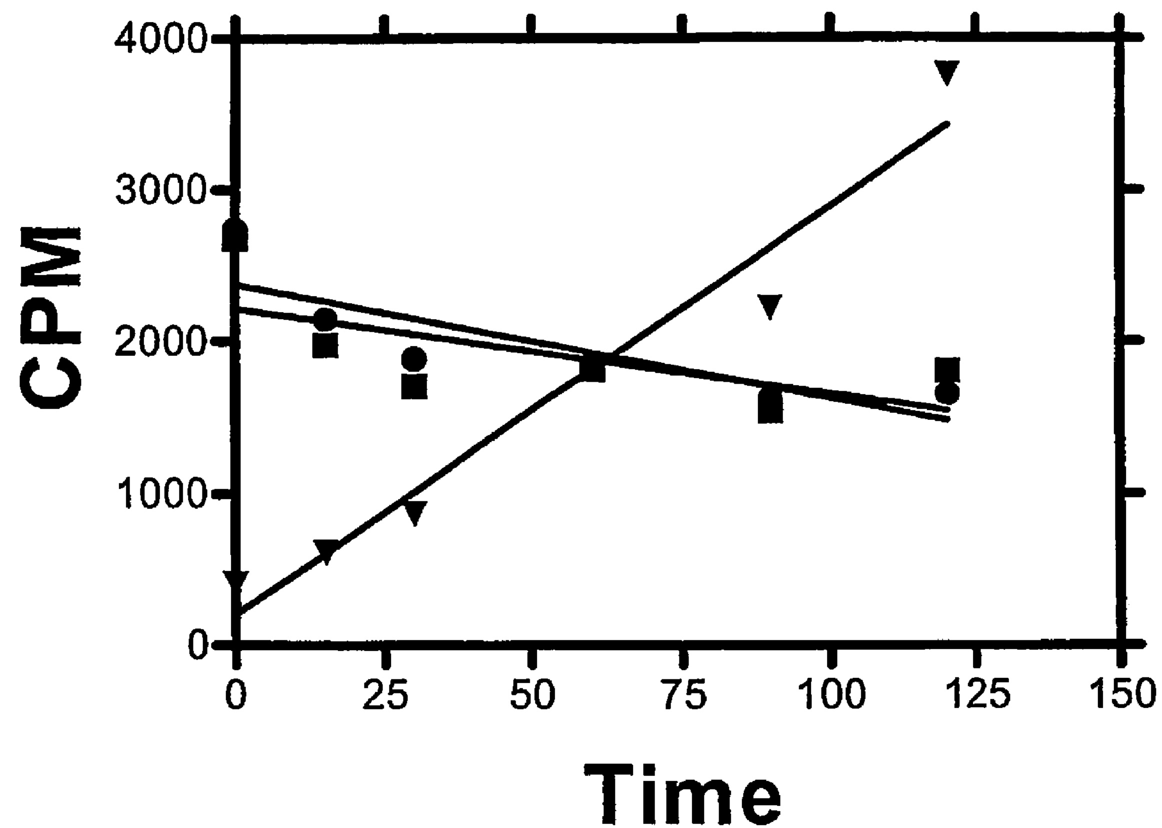
FIG. 1 shows the dTMP kinase activity (CPM) over time (0 to 120 minutes) of AT-TK1a (■), AT-TK1b (●) and HSV1-TK (▼), respectively.

The invention is further illustrated with reference to the following examples, which are not intended to be in any way limiting to the scope of the invention as claimed.

Example 1

Construction of a Retrovirus Vector Expressing Plant Kinases

The cDNA of plant kinases were cloned into a retrovirus vector based on the Moloney murine leukemia (MLV) virus to generate a replication-deficient recombinant retrovirus containing the TK1 kinases.

DNA fragments were amplified with Pfu polymerase (Stratagene) using primers with designed flanking restriction enzyme sites.

*Arabidopsis* constructs based on AT-TK1a were cut with BamHI/XhoI, and tomato PCR fragments were cut with BglII/XhoI, and cloned into the BglII-XhoI site of plasmid vector pLCXSN, which is a retroviral transfer vector derived from pLXSN (Clontech, cat# K1060-B) by insertion of the CMV promoter upstream of the polylinker.

Four constructs were obtained: AtTK1 (PZG53), AtTK1ΔC24 (PZG56), TomTK1 (PZG69) and TomTK1ΔC26 (PZG59). pLCXSN alone and the vector containing HSV1-TK (cloned into BamHI/XhoI site) were used as a control.

The plasmids were purified using the Qiagen plasmid kit (QIAGEN) and DNA sequences of the constructed plasmids were verified by DNA sequence determination.

The following primer sequences were used:

```
                            (AT TK1-for; SEQ ID NO: 14)
5' ccg ctc gag atg gcg act ctc aaa gct tcc ttt ttg
3';

                            (AT TK1-rev; SEQ ID NO: 15)
5' cgc gga tcc tta gat tgt agc agc aac aca gga ttc
3';

                             (AT TK1 DC; SEQ ID NO: 16)
5' cgc gga tcc tta aac aat atg att agt gat gta atg
ctt g 3';

                              (T TK1 DC; SEQ ID NO: 17)
5' gga aga tct tta gac aga ttg tcc att aac ata gtg
ctg 3';

                             (T TK1-rev; SEQ ID NO: 18)
5' gga aga tct tta tgg atc aac tag tgg tga ttc taa
g 3';
and

                             (T TK1-for; SEQ ID NO: 19)
5' ccg ctc gag atg gct ttt tca tca tct gct aga aac
3'.
```

For comparison an expression plasmid for human Herpes simplex virus type 1 thymidine kinase (HSV1-TK) was also constructed. The thymidine kinase from human HSV1 was amplified using the primers:

```
                          (HSV1-TK-for; SEQ ID NO: 20)
5' tat agg atc cgc cac cat ggc ttc gta ccc cgg c
3';
and

                          (HSV1-TK-rev; SEQ ID NO: 21)
5' tat act cga gga ggt cga ctc agt tag cc 3';
```

and using the plasmid pCMV-pacTK described by Karreman [Karreman C; *Gene* 1998 218 57-62] as template.

293T packaging cells (ATTC CRL-11268) were cultured at 37° C. in OPTIMEM 1 medium (Life Technologies, Inc.). The constructed pLCXSN plasmid vector was transfected into the packaging cells using LipofectAMINE PLUS (Life Technology Inc.) according to the protocol provided by the supplier. The medium from the transfected cells was collected 48 hours after transfection, filtered through a 0.45 mm filter, pelleted by ultracentrifugation (50,000×g, 90 minutes at 4° C.) and dissolved in TEN buffer (100 mM NaCl, 10 mM Tris pH 7.5, 1 mM EDTA).

The virus-containing buffer was subsequently used to transduce the cancer cell lines with MOI of 5.

Cell Culture and Retroviral Transduction

Glioblastoma U-87 MG (ATCC HTB-14), and glioblastoma U-118 MG (ATCC HTB-15) cells were purchased from the American Type Culture Collection. All cells were cultured in Minimum essential medium, E-MEM M (Bio Whittaker Cat. No. 12-611) with 10% (v/v) Australian originated fetal calf serum (Bio Whittaker Cat. No. 14-701) and 1 ml/l of gentamicin (Bio Whittaker Cat. No. 17-518 L). Cells were grown at 37° C. in a humidified incubator with a gas phase of 5% $CO_2$.

The cells lines were transduced with the retrovirus containing medium mixed with 5 μg/ml Polybrene, incubated for 48 hours and then cultured continuously for 3 weeks in the presence of 200 μg/ml geneticin (Life Technologies Inc.).

Cell Proliferation Assays

Cells were plated at 1500-2500 cells/well in 96-well plates coated with poly-L-lysine. AZT (3'-azido-3'-deoxythymidine; available from Sigma) was added after 24 hours, and the medium containing the nucleoside analogs was not changed.

Cell survival was assayed by the XTT assay (Roche) after 5 days of drug exposure.

Each experiment was performed in four replicates. The $IC_{50}$ value of the investigated compounds was calculated as the mean value of these experiments using SigmaPlot® (Dyrberg Trading, Karlslunde, D K) and calculated according to the expression:

$$d_I = \mathrm{Max}/(1+([I]/IC_{50}))$$

wherein $d_I$=cell growth at inhibitor concentration as determined by the XTT assay;

Max=maximal cell growth as determined by the XTT assay;

[I]=the inhibitory concentration; and $IC_{50}$=(50% growth inhibitory concentration) a dose that inhibits cell growth by 50%.

Expression of Plant Kinases of Increased Sensitivity to AZT

The sensitivity of the untransduced cells, and of the cells transduced with either the retroviral vector alone or the vector containing plant kinases for AZT, was determined.

The cytotoxicity ($IC_{50}$) was determined after 5 days of drug exposure. The results of this determination are presented in Table 4.

TABLE 4

Sensitivity ($IC_{50}$) of glioblastoma cell lines to AZT (mM)
The concentrations which cause 50% lethality are shown for the each construct and parental cell line. The factor of sensitivity increase is compared to the parental cell line.

| $IC_{50}$ | None | PZG53 | PZG56 | PZG59 | PZG69 | HSV1-TK | pLCXSN |
|---|---|---|---|---|---|---|---|
| Transient polyclonal cell lines | | | | | | | |
| U-87 MG | 4.468 | 0.097 | 0.303 | 0.026 | 0.047 | >5 | >5 |
| U-118 MG | 1.021 | 0.062 | 0.296 | 0.034 | 0.045 | 1.923 | 0.859 |
| Stable polyclonal cell lines | | | | | | | |
| U-87 MG | 2.439 | 0.0719 | 0.1324 | 0.0251 | 0.017 | 2.577 | 4.0676 |
| U-118 MG | 0.779 | 0.095 | 0.2027 | 0.0266 | 0.1902 | 2.7264 | 2.3335 |

The difference in sensitivity between the parental cell lines and the cells transduced with the pLCXSN vector alone was less than 1-fold. Both glioblastoma cell lines, that expressed plant kinases, showed an increase in sensitivity to AZT. The highest increase was detected for the U-87 MG cell line expressing tomato TK1 with an almost 240-fold decrease in $IC_{50}$ compared with the untransduced cells.

Example 2

Cloning of Thymidine Kinases

This example describes how the genes encoding the tomato, pine, rice and thale cress thymidine kinases of the invention were identified, and how vectors to express various thymidine kinases were constructed.

Based on their homology to the human TK1, two sequences from tomato, ACCN BE463259 and ACCN BG129197 (available from the Clemson University Genomics Institute, USA), a sequence from pine, ACCN AW755132 (available from Dr. Ross Whetten, North Carolina State University, USA), and an EST, ACCN D24903 (available from the MAFF DNA Bank, 1-2, 2-chome, Kannondai, Tsukuba, Ibaraki 305-8602, Japan) with homology to the postulated TK1 from rice (ACCN AF066050) were identified using the local homology search tool (tBLASTn) available from the NCBI web-site, and using the standard settings (i.e. Filter on, Expect=10, Word size=3, Matrix=Blosum62, Gap costs=Existence 11 Extension 1).

Starting from plasmid-derived primers the inserts were sequenced. Subsequently primers were designed based on the newly obtained sequence data. The sequence of the insert in D24903 combined with sequence information derived from ACCN AU068889 predicted an ORF for a 64 amino acids longer protein than reported in AF066050.

Tomato Thymidine Kinase

The ORF of the tomato thymidine kinase was amplified by PCR using the following primers:

```
                                (1MS TOTK1-B; SEQ ID NO: 22)
5' CGC GGA TCC ATG GCT TTT TCA TCA TCT GCT AGA AAC
CCA GTT GAC CTG AG 3';
and

                                (2MS TOTK1-E; SEQ ID NO: 23)
5' CCG GAA TTC TTA TGG ATC AAC TAG TGG TGA TTC TAA
G 3';
and
```

using the plasmid containing ACCN BG129197 as the template.

The PCR fragment was subsequently cut by EcoRI/BamHI and ligated into pGEX-2T vector (Amersham-Pharmacia), that was also cut by EcoRI/BamHI. The resulting plasmid was named pGEX-2T-TOM-TK1

*Arabidopsis thaliana* Thymidine Kinase (AT-TK1a)

The ORF of TK1a from *Arabidopsis thaliana* (Accession No. AAF13097) was amplified from a cDNA library (Stragene) using the following primers:

```
                                 (1msAtTK1-B; SEQ ID NO: 24)
5' CGC GGA TCC ATG GCG ACT CTC AAA GCT TCC TTT TTG
ATC AAA ACC C 3';
and

                                 (2msAtTK1-E; SEQ ID NO: 25)
5' CCG GAA TTC TTA GAT TGT AGC AGC AAC ACA GGA TTC
AGC 3'.
```

The PCR fragment was subsequently cut by EcoRI/BamHI and ligated into pGEX-2T vector (Amersham-Pharmacia) that was also cut by EcoRI/BamHI. The resulting plasmid was named pGEX-2T-AT-TK1a.

*Arabidopsis thaliana* Thymidine Kinase (AT-TK1b)

The ORF of TK1b from *Arabidopsis thaliana* (Accession No. BAB09824) was amplified from a cDNA library (Stragene) using the following strategy, which also created several N-terminal deleted mutants of AT-TK1b.

The full length ORF (ACCN BAB09824) was amplified from a cDNA library (Stratagene) using the primers:

```
                                  (1mtAtTK1L; SEQ ID NO: 26)
5' ATG AGA ACA TTA ATC TCA CCA TCT C 3';
and

                                  (2mtAtTK1L; SEQ ID NO: 27)
5' CTA AAG TGA ACT TGC TAC AAC ACT ATG 3'.
```

This full length PCR product was used for amplification of a fragment with BamHI/EcoRI overhangs using the primers

```
                                 (1mtAtTK1L-B; SEQ ID NO: 28)
5' CGC GGA TCC ATG AGA ACA TTA ATC TCA CCA TCT C
3';
and

                                  (2mtAtTK1-E; SEQ ID NO: 29)
5' CCG GAA TTC CTA AAG TGA ACT TGC TAC AAC AC 3'.
```

The PCR fragment was subsequently cut by EcoRI/BamHI and ligated into pGEX-2T vector that was also cut by EcoRI/BamHI. The resulting plasmid was named pGEX-2T-AT-TK1b (P661).

In analogy N-terminal deletions were made and ligated into pGEX-2T. An N-terminal deletion of 22 amino acids was achieved by using the primers

```
                                 (1mtAtTK1I-B; SEQ ID NO: 30)
5' CGC GGA TCC TCC ACC GCT CTT CGC TTC TCC 3';
and
```

2mtAtTK1-E (SEQ ID NO: 29).

The resulting plasmid was named pGEX-2T-AT-ΔN22TK1b (P662).

An N-terminal deletion of 45 amino acids was achieved by using the primers

```
                                  (1mtAtTK1-B; SEQ ID NO: 31)
5' CGC GGA TCC TCC ACC AGA AAG CTA CAA ACG 3';
and
```

2mtAtTK1-E (SEQ ID NO: 29).

The resulting plasmid was named pGEX-2T-AT-ΔN45TK1b (P663).

An N-terminal deletion of 63 amino acids was achieved by using the primers

```
                                 (1mtATTK1S-B; SEQ ID NO: 32)
5' CGC GGA TCC CAG CCG CTC TCC TCC TCA TC 3';
and
```

2mtAtTK1-E (SEQ ID NO: 29).

The resulting plasmid was named pGEX-2T-AT-ΔN63TK1b (P664).

Rice Thymidine Kinase

The thymidine kinase from rice was amplified using the primers

```
                                 (1osTK1s-B; SEQ ID NO: 33)
5' CGG GAT CCG GCG GCG GCG GCG GAC AAG TCT CG 3';
and

                                 (2osTK1-E; SEQ ID NO: 34)
5' CGG AAT TCT TAC TTG AAA GCA TGG ATA ACC TTG G
3';
```

and using D24903 as a template.

The PCR fragment was subsequently cut by EcoRI/BamHI and ligated into pGEX-2T vector (available from Amersham-Pharmacia) that was also cut by EcoRI/BamHI. The resulting plasmid was named pGEX-2T-Rice-TK1.

HSV1 Thymidine Kinase (Used for Control)

The thymidine kinase from HSV1 was amplified using the primers

```
                                (HSV1-for A; SEQ ID NO: 35)
5' CGC GGA TCC ATG GCT TCG TAC CCC GGC CAT C 3';
and

                                  (HSV1-rev; SEQ ID NO: 36)
5' CCG GAA TTC TTA GTT AGC CTC CCC CAT CTC CCG 3';
```

and using the plasmid pCMV-pacTK described by Karreman [Karreman C; *Gene* 1998 218 57-62] as template.

The PCR fragment was subsequently cut by EcoRI/BamHI and ligated into pGEX-2T vector (Amersham-Pharmacia) that was also cut by EcoRI/BamHI.

The resulting plasmid was named pGEX-2T-HSV1-TK.

Example 3

Expression and Purification of Recombinant Thymidine Kinases

This example describes how KY895 were transformed with the plasmids obtained according to Example 2, in order to express thymidine kinases.

KY895 cells were transformed by the expression plasmids of Example 2 using standard techniques, e.g. as described by e.g. Sambrook et al. [Sambrook et al.; *Molecular Cloning: A Laboratory Manual*, Cold Spring Harbor Lab., Cold Spring Harbor, N.Y. 1989].

Transformed KY895 were grown to an OD600 nm of 0.5-06 in LB/Ampicillin (100 μg/ml) medium at 37° C. and protein expression was induced by addition of IPTG to make 100 μM. The cells were further grown for 4 h at 25° C. and subsequently harvested by centrifugation. The cell pellet was subjected to sonification in the binding buffer A (20 mM $NaPO_4$ pH 7.3; 150 mM NaCl; 10% Glycerol; and 0.1% Triton X-100) in presence of a protease inhibitor cocktail (Complete™—EDTA free from Roche Diagnostics).

The ability of the extracts to phosphorylate the four natural deoxyribonucleoside was tested at a fixed concentration of 100 μM of the deoxyribonucleosides. The highest specific activity in each extract was set to 100%. In (parenthesis) the specific activity corresponding to 100% is given in mU/mg.

The results of these evaluations are presented in Table 5.

TABLE 5

Deoxyribonucleoside Kinase Activity in Extracts of KY895 Cells 4 hours of induction with 0.1 mM IPTG at 25° C.

| KY895 transformed with | Thd | dAdo | dGuo | dCyd |
|---|---|---|---|---|
| pGEX-2T | n.d. | n.d. | n.d. | n.d. |
| pGEX-2T-TOM-TK1 | 100 (124) | n.d. | n.d. | 0.1 |
| pGEX-2T-AT-TK1a | 100 (53) | n.d. | n.d. | n.d. |
| pGEX-2T-AT-TK1b | 100 (4.4) | n.d. | n.d. | 4 |
| pGEX-2T-AT-ΔN22TK1b | 100 (4.4) | n.d. | n.d. | 4 |
| pGEX-2T-AT-ΔN45TK1b | 100 (5.2) | n.d. | n.d. | 3 |
| pGEX-2T-AT-ΔN63TK1b | 100 (4) | n.d. | n.d. | 1 |

n.d. designates "not detectable".

The data in this table show that all enzymes are thymidine kinases.

The extracts were subjected to centrifugation at 10,000×g for 30 minutes, filtered, and loaded onto the column. Thereafter two 1 ml Glutathione-Sepharose columns (available from Pharmacia) were combined and equilibrated in binding buffer A. After loading of the sample, the column was washed with 40 ml of binding buffer A. Subsequently the column was washed with 5 ml 10 mM ATP/$MgCl_2$ in (A) and incubated for 1 hour at room temperature, and then 30 minutes at 4° C. ATP/$MgCl_2$ was removed by washing with 10 ml binding buffer A.

The GST-tag protein is cleaved from the TK on the GST binding column by thrombin cleavage according to the manufacturers protocol (Pharmacia).

The kinetic constants of the purified TK were determined as described by Munch-Petersen et al. [Munch-Petersen B, Knecht W, Lenz C, Søndergaard L, Piškur J: Functional expression of a multisubstrate deoxyribonucleoside kinase from *Drosophila melanogaster* and its C-terminal deletion mutants; *J. Biol. Chem.* 2000 275 6673-6679].

Kinetic data were evaluated by nonlinear regression analysis using the Michaelis-Menten equation $v=V_{max}\times[S]/(K_m+[S])$ or Hill-equation $v=V_{max}\times[S]^h/(K_{0.5}{}^h+[S]^h)$ as described by Knecht et al. [Knecht W, Bergjohann U, Gonski S, Kirschbaum B & Löffler M: Functional expression of a fragment of human dihydroorotate dehydrogenase by means of the baculovirus expression vector system and kinetic investigation of the purified recombinant enzyme; *Eur. J. Biochem.* 1996 240 292-301]. $K_m$ is the Michaelis constant, $K_{0.5}$ defines the value of the substrate concentration [S] at which $v=0.5\ V_{max}$ and h is the Hill coefficient [Cornish-Bowden A: Fundamentals of enzyme kinetics; Portland Press Ltd., London, 1995, pp. 33; and Liebecg C: IUBMB Biochemical nomenclature and related documents; Portland Press Ltd., London, 1992].

TABLE 6

Relation between Velocity and Substrate Concentration for Thd for Recombinant (r) Plant Kinases.

| | $K_m$ (μM) | $V_{max}$ (mU/mg) | $k_{cat}$ ($s^{-1}$) | $k_{cat}/K_m$ ($M^{-1}\ s^{-1}$) |
|---|---|---|---|---|
| rTOM-TK1 | 0.8 | 60 | 0.026 | 32500 |
| rAT-ΔN45TK1b* | 18 | 165 | 0.071 | 3944 |
| rAT-TK1a* | 85 | 452 | 0.2 | 2353 |
| rHSV1-TK** | 0.38 | — | 0.46 | 1200000 |

*Data from Le Breton C: In-vitro study of novel deoxyribonucleoside kinases for gene therapy; B. Sc. Report, 2002, University of Paris VII/Technical University of Denmark.

**Data from Kokoris M S and Black M E: Characterization of Herpes Simplex Virus type 1 thymidine kinase mutants engineered for improved ganciclovir or acyclovir activity; Protein Science 2002 11 2267-2272.

TABLE 7

Relation between Velocity and Substrate Concentration for AZT for Recombinant Plant Kinases

| | $K_m$ (μM) | $V_{max}$ (mU/mg) | $k_{cat}$ ($s^{-1}$) | $k_{cat}/K_m$ ($M^{-1} s^{-1}$) |
|---|---|---|---|---|
| rTOM-TK1 | 22.4 | 1579 | 0.681 | 30400 |
| rAT-ΔN45TK1b | 1.46 | 242 | 0.104 | 71200 |
| rAT-TK1a | 3.55 | 244 | 0.106 | 29900 |
| rHSV1-TK | 1.7 | 4.1 | 0.028 | 16500 |

Tables 6 and 7 demonstrate that plant TK's phosphorylate AZT more efficiently ($k_{cat}/K_m$) than Thd, which is in sharp contrast to the rHSV1-TK which phosphorylates Thd far more efficiently than AZT. The ratio $[k_{cat}/K_m$ (Thd)]/[$k_{cat}/K_m$ (AZT)] for the tomato, *Arabidopsis* and HSV1-TKs are as follows:

| | |
|---|---|
| rTOM-TK1 | 1.07 |
| rAT-ΔN45TK1b | 0.06 |
| rAT-TK1a | 0.08 |
| rHSV1-TK | 72.7 |

Example 4

Growth of Transformed *E. coli* KY895 on Nucleoside Analog Plates

This example describes how host cells transformed with the plasmids obtained according to Example 2 are able to grow on plates in presence of the nucleoside analog AZT (3'-azido-3'-deoxythymidine).

The experiment was carried out as described by Knecht et al. [Knecht, W., Munch-Petersen, B. & Piškur, J.: Identification of residues involved in the specificity and regulation of the highly efficient multisubstrate deoxyribonucleoside kinase from *Drosophila melanogaster; J. Mol. Biol.* 2000 301 827-837].

TABLE 8

Growth of KY895 Cells in Presence of AZT

| KY895 transformed with | $LD_{100}$ (μM) |
|---|---|
| pGEX-2T | >100 |
| pGEX-2T-TOM-TK1 | 0.0316 |
| pGEX-2T-AT-TK1a | 0.316 |
| pGEX-2T-AT-TK1b | 1 |
| pGEX-2T-AT-ΔN22TK1b | 0.316 |
| pGEX-2T-AT-ΔN45TK1b | 0.1 |
| pGEX-2T-AT-ΔN63TK1b | 0.1 |
| pGEX-2T-HSV1-TK | 1 |
| pGEX-2T-hu-TK1 | 1 |
| pGEX-2T-Bm-dNK | 100 |
| pGEX-2T-Dm-dNK | 100 |

pGEX-2T is the vector and is available from Amersham-Pharmacia;

pGEX-2T-Dm-dNK is the vector containing the gene encoding a multisubstrate deoxyribonucleoside kinase derived from *Drosophila melanogaster* described by Munch-Petersen et al. [Munch-Petersen B, Knecht W, Lenz C, SØndergaard L, Piskur J: Functional expression of a multisubstrate deoxyribonucleoside kinase from *Drosophila melanogaster* and its C-terminal deletion mutants; J. Biol. Chem. 2000 275 6673-6679];

pGEX-2T-Bm-dNK is the vector containing the gene encoding a deoxyribonucleoside kinase derived from *Bombyx mori* described by Knecht et al. [Knecht W, Ebert Petersen G, Munch-Petersen B, Piskur J: Deoxyribonucleoside kinases belonging to the thymidine kinase 2 (TK2)-like group vary significantly in substrate specificity, kinetics and feed-back regulation; J. Mol. Biol. 2002 315 529-540];

pGEX-2T-huTK1 is the vector containing the gene encoding a human thymidine kinase (TK1) described by Berenstein et al. [Berenstein D, Christensen J F, Kristensen T, Hofbauer R, Munch-Petersen B: Valine, not methionine, is amino acid 106 in human cytosolic thymidine kinase (TK1). Impact on oligomerization, stability, and kinetic properties; J. Biol. Chem. 2000 275 (41) 32187-32192].

Table 8 shows that the thymidine kinase derived from tomato is the most potent kinase when determined in combination with the nucleoside analog AZT. This enzyme is about 30 times as active as that derived from Herpes simplex.

Example 5

Testing for TK Activity on TK Selection Plates

This example describes determination of thymidine kinase activity using KY895 cells transformed with the plasmids described in Example 2.

The test for thymidine kinase activity was carried out as described by Knecht et al. [Knecht, W., Munch-Petersen, B. & Piškur, J.: Identification of residues involved in the specificity and regulation of the highly efficient multisubstrate deoxyribonucleoside kinase from *Drosophila melanogaster; J. Mol. Biol.* 2000 301 827-837].

pGEX-2T is the vector available from Amersham-Pharmacia used as control.

The multisubstrate deoxyribonucleoside kinase from the fruitfly *Drosophila melanogaster* (pGEX-2T-Dm-dNK), obtained according to Munch-Petersen et al. [Munch-Petersen B, Knecht W. Lenz C, Søndergaard L, Piškur J: Functional expression of a multisubstrate deoxyribonucleoside kinase from *Drosophila melanogaster* and its C-terminal deletion mutants; *J. Biol. Chem.* 2000 275 6673-6679] was used as a positive control.

TABLE 9

Growth on TK Selection Plates

| | Thymidine (μg/ml) | | | | | |
|---|---|---|---|---|---|---|
| | 0.05 | 1 | 2 | 10 | 20 | 50 |
| pGEX-2T | – | – | – | – | – | – |
| pGEX-2T-Dm-dNK | + | + | + | + | + | + |
| pGEX-2T-TOM-TK1 | + | + | + | + | + | + |
| pGEX-2T-Rice-TK1 | n.d. | n.d. | + | n.d. | n.d. | n.d. |
| pGEX-2T-AT-TK1a | n.d. | n.d. | + | n.d. | n.d. | n.d. |

+ growth
– no growth
n.d. not determined

This example demonstrates that all enzymes are able to phosphorylate thymidine.

Example 6

Phosphorylation of Nucleoside Monophosphates to Nucleoside Diphosphates

Monophosphate kinase activity was tested by determining the products of the thymidine kinase catalyzed reactions, essentially as described by Munch-Petersen et al.; *J. Biol. Chem.* 1998 273 7 3926-3931.

Briefly, the amount of enzyme catalyzing the conversion of 30 nmol/min of thymidine to thymidine monophosphate (30 mU) was incubated in 100 μl of a mixture of 50 mM Tris-HCl, pH 8.0 (22° C.); 2.5 mM $MgCl_2$; 2.5 mM ATP; 10 mM dithiothreitol; 0.5 mM CHAPS; 3 mg/ml of bovine serum albumin; and 100 μM 3H-labelled substrate (1.8 Ci/mmol).

Time samples of 5 μl reaction mixture were mixed with 5 μl 5 mM thymidine, TMP, TDP and TTP. 5 μl, of this mixture were plated on polyethylenimine-cellulose plates, which were developed ascending in 0.5 M $LiCl_2$. The spots with the nucleosides and nucleotides were identified under UV light and cut out.

The radioactivity in the spots was extracted with 0.2 M KCl in 0.1 M HCl, and determined by liquid scintillation counting. 1 pmol radioactive nucleoside/tide counts 850 cpm.

Recombinant thymidine kinases were expressed and purified as described in Example 3.

Figure 2:
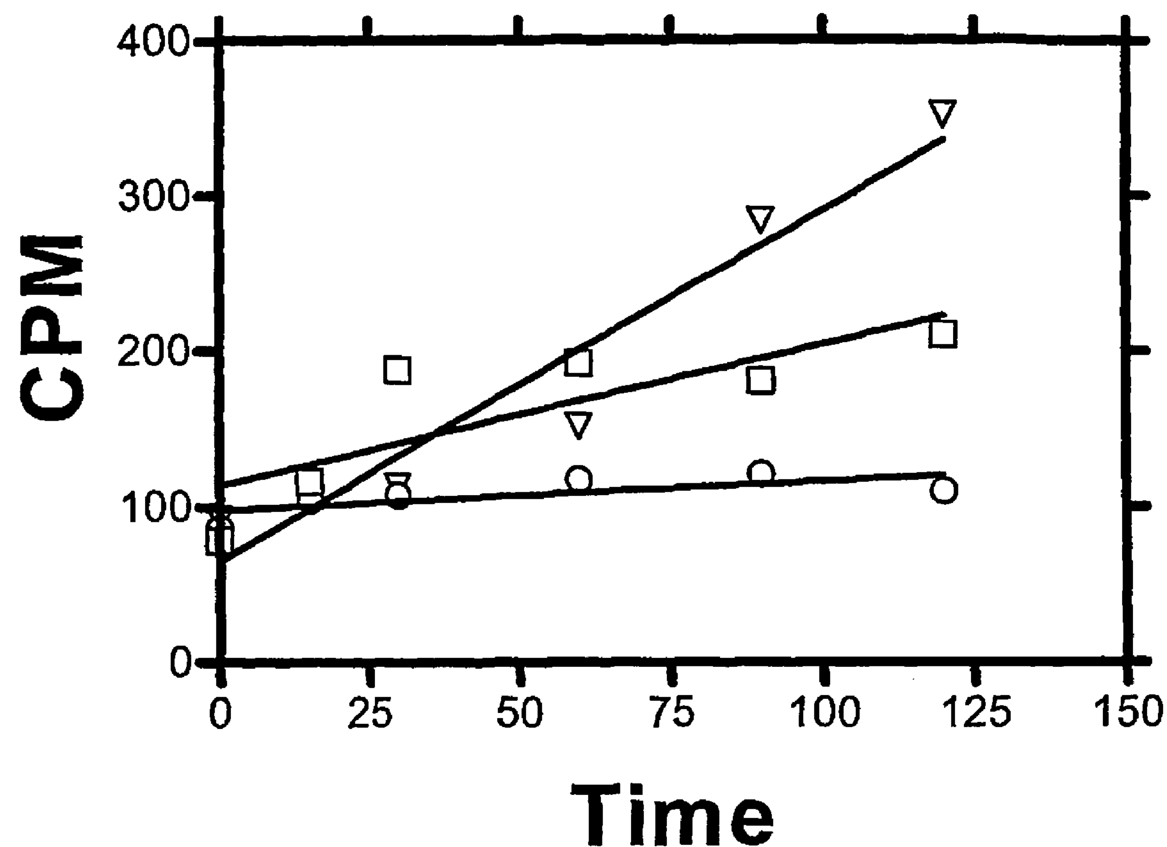
FIG. 2 shows AZT monophosphate kinase activity (CPM) (0 to 120 minutes) of AT-TK1a (□), AT-TK1b (○) and HSV1-TK (∇), respectively.

The results of this experiment are presented in FIGS. 1 and 2. The cpm obtained at the indicated times (15, 30, 60, 90 and 120 minutes, respectively) are determined in the TDP spots derived from 2.5 μl of the reaction mixture.

As expected, HSV1-TK phosphorylates both substrates, but the AZT-monophosphate substrate is phospholylated at a 10 fold lower degree than the thymidine substrate. Surprisingly, however, is that the plant TK1 enzymes are capable of phosphorylating AZT-monophosphate although they are unable to phosphorylate TMP. This new property has never before been reported for any thymidine kinase.

The invention claimed is:

1. A vector comprising a polynucleotide coding sequence, operably linked to a promoter functional in mammalian cells, said polynucleotide coding sequence encoding a polypeptide comprising an amino acid sequence which (a) is at least 90% identical to SEQ ID NO:4, with the percentage identity determined over the entire length of SEQ ID NO:4, or (b) differs from SEQ ID NO:4 solely by a C-terminal deletion of 1-30 amino acid residues and/or N-terminal deletion of 22 amino acid residues, wherein said polypeptide has thymidine kinase enzyme activity.

2. The vector of claim 1, wherein said polypeptide differs from SEQ ID NO:4, if at all, solely by (A) one or more conservative substitutions, (B) C-terminal deletion of 1-30 amino acid residues, and/or (C) N-terminal deletion of 22 amino acid residues, with the proviso that it does not differ by all of (A)-(C), wherein each such conservative substitution being (1) the substitution of an amino acid selected from the group of non-polar residues consisting of alanine, leucine, isoleucine, valine, proline, methionine, phenyalalanine and tryptophan with another amino acid of the same group, (2) the substitution of an amino acid selected from the group of neutral polar residues consisting of serine, threonine, tyrosine, asparagine, glutamine and cysteine with another amino acid of the same group, (3) the substitution of an amino acid selected from the group consisting of lysine, arginine and histidine with another amino acid of the same group, or (4) the substitution of aspartic acid with glutamic acid, or vice versa.

3. The vector of claim 1, wherein said polypeptide (a) is at least 95% identical to SEQ ID NO:4, wherein the percentage identity determined over the entire length of SEQ ID NO:4, or (b) differs from SEQ ID NO:4, if at all, solely by (A) one or more conservative substitutions, (B) C-terminal deletion of 1-30 amino acid residues, and/or (C) N-terminal deletion of 22 amino acid residues, with the proviso that it does not differ by all of (A)-(C), wherein each such conservative substitution being (1) the substitution of an amino acid selected from the group of non-polar residues consisting of alanine, leucine, isoleucine, valine, proline, methionine, phenyalalanine and tryptophan with another amino acid of the same group, (2) the substitution of an amino acid selected from the group of neutral polar residues consisting of serine, threonine, tyrosine, asparagine, glutamine and cysteine with another amino acid of the same group, (3) the substitution of an amino acid selected from the group consisting of lysine, arginine and histidine with another amino acid of the same group, or (4) the substitution of aspartic acid with glutamic acid, or vice versa.

4. The vector of claim 1, said polypeptide comprises an amino acid sequence which is at least 95% identical to SEQ ID NO:4, with the percentage identity determined over the entire length of SEQ ID NO:4.

5. The vector of claim 1, wherein said polypeptide comprises an amino acid sequence which is identical to SEQ ID NO:4, or which differs from SEQ ID NO:4 solely by a C-terminal deletion of 1-30 amino acid residues.

6. The vector of claim 1, wherein said polypeptide comprises an amino acid sequence which is identical to SEQ ID NO:4, or which differs from SEQ ID NO:4 solely by a C-terminal deletion of 1-26 amino acid residues.

7. The vector of claim 1, said polypeptide comprises an amino acid sequence which is identical to SEQ ID NO:4, or which differs from SEQ ID NO:4 solely by a C-terminal deletion of 1-24 amino acid residues.

8. The vector of claim 1, said polypeptide comprises an amino acid sequence which is identical to SEQ ID NO:4, or which differs from SEQ ID NO:4 solely by a C-terminal deletion of 24 amino acid residues.

9. The vector of claim 1, said polypeptide comprises an amino acid sequence which is identical to SEQ ID NO:4, or which differs from SEQ ID NO:4 solely by an N-terminal deletion of 22 amino acid residues.

10. The vector of claim 1, wherein said polypeptide has no deletion in a residue identified by Table 1 as a conserved residue.

11. A packaging cell line transformed with the vector according to claim 1.

12. A transformed host cell comprising the vector according to claim 1.

13. A composition comprising the isolated vector according to claim 1.

14. The composition of claim 13, wherein said polypeptide comprises one or more of the following motifs/regions:

```
Val Ile Gly Ile Asp Glu Ala Gln Phe    (Motif I)
Phe (amino acids 90-99 of SEQ ID NO:
1),

Val Ala Gly Leu Asp Gly                (Motif II)
(amino acids 119-124 of SEQ ID NO: 1),

Tyr Met Pro Val Cys Arg                (Motif III)
(amino acids 179-184 of SEQ ID NO: 1),
and

Val A1 Lys Leu A2 A3 Arg Cys Glu A4    (Lid region),
(SEQ ID NO: 37),
```

wherein A1 is selected from Thr and Val, A2 is selected from Thr and Lys, A3 is selected from Ala and Set, and A4 is selected from Leu and Val.

15. The composition of claim 13, wherein said polypeptide comprises all of the conserved residues identified in Table 1.

16. The composition of claim 13, wherein said polypeptide differs from SEQ ID NO:4 by a C-terminal deletion of 1-30 amino acid residues.

17. The composition of claim 16, wherein said polypeptide differs from SEQ ID NO:4 by a C-terminal deletion of 26 amino acid residues (thereby having the amino acid sequence of SEQ ID NO: 5).

18. The composition of claim 13, wherein said polypeptide decreases at least three (3) fold the lethal dose (LD100) of AZT when compared to the action of a thymidine kinase derived from human Herpes simplex virus type 1 thymidine kinase (HSV1-TK).

19. The composition of claim 13, wherein the polypeptide is at least 90% identical to SEQ ID NO:4, with the percentage identity determined over the entire length of SEQ ID NO:4.

20. The composition of claim 13, wherein the polypeptide is at least 95% identical to SEQ ID NO:4, with the percentage identity determined over the entire length of SEQ ID NO:4.

21. The composition of claim 13, wherein polypeptide is at least 98% identical to SEQ ID NO:4, with the percentage identity determined over the entire length of SEQ ID NO:4.

22. The composition of claim 13, wherein the polypeptide is identical to SEQ ID NO:4.

23. The composition of claim 13, wherein the polypeptide comprises at least one of the following:

a first subsequence identical to motif I (amino acids 105-114 of SEQ ID NO:4), a second subsequence identical to motif II (amino acids 134-139 of SEQ ID NO:4), a third subsequence identical to motif III (amino acids 194-199 of SEQ ID NO:4).

24. The composition of claim 13, further comprising a pharmaceutically acceptable carrier or diluent.

25. The composition of claim 13, further comprising at least one nucleoside analogue.

26. The composition of claim 25, wherein the at least one nucleoside analogue is 3'-azido-3'-deoxythymidine (AZT) monophosphate and/or AZT.

27. The composition of claim 13, wherein said polypeptide differs from SEQ ID NO:4, if at all, solely by (A) one or more conservative substitutions, (B) C-terminal deletion of 1-30 amino acid residues, and/or (C) N-terminal deletion of 22 amino acid residues, with the proviso that it does not differ by all of (A)-(C), wherein each such conservative substitution being (1) the substitution of an amino acid selected from the group of non-polar residues consisting of alanine, leucine, isoleucine, valine, proline, methionine, phenyalalanine and tryptophan with another amino acid of the same group, (2) the substitution of an amino acid selected from the group of neutral polar residues consisting of serine, threonine, tyrosine, asparagine, glutamine and cysteine with another amino acid of the same group, (3) the substitution of an amino acid selected from the group consisting of lysine, arginine and histidine with another amino acid of the same group, or (4) the substitution of aspartic acid with glutamic acid, or vice versa.

28. The composition of claim 27, wherein the polypeptide differs from SEQ ID NO:4, if at all, solely by one or more conservative substitutions.

29. The composition of claim 27, wherein the polypeptide differs from SEQ ID NO:4, if at all, solely by a single conservative substitution.

30. The composition of claim 13, wherein said polypeptide (aa) is at least 95% identical to SEQ ID NO:4, with the percentage identity determined over the entire length of SEQ ID NO:4, or (bb) differs from SEQ ID NO:4, if at all, solely by (A) one or more conservative substitutions, (B) C-terminal deletion of 1-30 amino acid residues, and/or (C) N-terminal deletion of 22 amino acid residues, with the proviso that it does not differ by all of (A)-(C), wherein each such conservative substitution being (1) the substitution of an amino acid selected from the group of non-polar residues consisting of alanine, leucine, isoleucine, valine, proline, methionine, phenyalalanine and tryptophan with another amino acid of the same group, (2) the substitution of an amino acid selected from the group of neutral polar residues consisting of serine, threonine, tyrosine, asparagine, glutamine and cysteine with another amino acid of the same group, (3) the substitution of an amino acid selected from the group consisting of lysine, arginine and histidine with another amino acid of the same group, or (4) the substitution of aspartic acid with glutamic acid, or vice versa.

31. The composition of claim 13, wherein said polypeptide of (a) comprises a first subsequence identical to motif I of SEQ ID NO:4 (amino acids 105-114 of SEQ ID NO:4), a second subsequence identical to motif II of SEQ ID NO:4 (amino acids 134-139 of SEQ ID NO:4), and a third subsequence identical to motif III of SEQ ID NO:4 (amino acids 194-199 of SEQ ID NO:4), wherein the spacing between the first and second subsequences being the same as between motif I and motif II in SEQ ID NO:4, and the spacing between the second and third subsequences being the same as between motif II and motif III in SEQ ID NO:4.

32. The composition of claim 31, said polypeptide of (a) further comprises a fourth subsequence of Val-(Thr/Val)-Lys-Leu-(Thr/Lys)-(Ala/Ser)-Arg-Cys-Glu-(Leu/Val) (SEQ ID NO:37), wherein the spacing between the third and fourth subsequences being the same as between motif III and the Lid region in SEQ ID NO:4, wherein the Lid region is the amino acids 159-168 of SEQ ID NO:4.

33. The composition of claim 32, the fourth subsequence being identical to the Lid region in SEQ ID NO:4.

34. A vector comprising a polynucleotide coding sequence, operably linked to a promoter functional in mammalian cells, said polynucleotide coding sequence encodes a polypeptide comprising an amino acid sequence which is at least 90% identical to SEQ ID NO:5, with the percentage identity determined over the entire length of SEQ ID NO:5, wherein said polypeptide has thymidine kinase enzyme activity.

35. A composition comprising the isolated vector according to claim 34.

36. The composition of claim 35, wherein said polypeptide comprises an amino acid sequence which is at least 95% identical to SEQ ID NO:5, with the percentage identity determined over the entire length of SEQ ID NO:5.

37. The composition of claim 35, wherein said polypeptide comprises an amino acid sequence which is at least 98% identical to SEQ ID NO:5, with the percentage identity determined over the entire length of SEQ ID NO:5.

38. The composition of claim 35, wherein said polypeptide comprises the amino acid sequence identical to SEQ ID NO:5.

39. The composition of claim 35, wherein said polypeptide comprising an amino acid sequence which is at least 90% identical to SEQ ID NO:5 differs from SEQ ID NO:5, if at all, solely by one or more conservative substitutions.

40. The composition of claim 35, wherein said polypeptide comprising an amino acid sequence which is at least 90% identical to SEQ ID NO:5 differs from SEQ ID NO:5, if at all, solely by a single conservative substitution.

41. The composition of claim 35, further comprising a pharmaceutically acceptable carrier or diluent.

42. The composition of claim 35, further comprising a nucleoside analogue.

43. A packaging cell line transformed with the vector according to claim 34.

44. A transformed host cell comprising the vector according to claim 34.

* * * * *

SEQUENCE LISTING

```
<160> NUMBER OF SEQ ID NOS: 37

<210> SEQ ID NO 1
<211> LENGTH: 660
<212> TYPE: DNA
<213> ORGANISM: Pinus taeda
<220> FEATURE:
<221> NAME/KEY: CDS
<222> LOCATION: (1)..(660)

<400> SEQUENCE: 1

atg gat gac tcg ggt atc tac aca agt gga gaa att cat ctt atc ttg       48
Met Asp Asp Ser Gly Ile Tyr Thr Ser Gly Glu Ile His Leu Ile Leu
1               5                   10                  15

ggg cct atg ttc gcg ggc aag acg act gcc ctt att cgt aaa atg cga       96
Gly Pro Met Phe Ala Gly Lys Thr Thr Ala Leu Ile Arg Lys Met Arg
            20                  25                  30

gca gaa att caa atg ggc aga aga gtg gtg ctt gtg aaa tct gac aag      144
Ala Glu Ile Gln Met Gly Arg Arg Val Val Leu Val Lys Ser Asp Lys
        35                  40                  45

gat aca aga tat ggg ctg aac tca gtt gtg tct cat gat ggt gca aaa      192
Asp Thr Arg Tyr Gly Leu Asn Ser Val Val Ser His Asp Gly Ala Lys
    50                  55                  60

atg cct tgc tgg gct gtt gca gat ctt gca tct ttc aaa ggc aaa tta      240
Met Pro Cys Trp Ala Val Ala Asp Leu Ala Ser Phe Lys Gly Lys Leu
65                  70                  75                  80

gga gag gag gct tac aag cag gta gat gtg atc ggc att gat gaa gca      288
Gly Glu Glu Ala Tyr Lys Gln Val Asp Val Ile Gly Ile Asp Glu Ala
                85                  90                  95

cag ttc ttc aaa gac ctg tat agt ttt tgt cag gta gca gct gat aga      336
Gln Phe Phe Lys Asp Leu Tyr Ser Phe Cys Gln Val Ala Ala Asp Arg
            100                 105                 110

gat ggg aaa att gtt att gtt gct ggc ctt gat ggg gat tat ttg agg      384
Asp Gly Lys Ile Val Ile Val Ala Gly Leu Asp Gly Asp Tyr Leu Arg
        115                 120                 125

aag agc ttt gga tca gct ctt gag ttg ata cct ata gcg gat tct gta      432
Lys Ser Phe Gly Ser Ala Leu Glu Leu Ile Pro Ile Ala Asp Ser Val
    130                 135                 140

gtt aaa ttg aag tca cgc tgt gag ctg tgt ggt aag gcc gca tca ttt      480
Val Lys Leu Lys Ser Arg Cys Glu Leu Cys Gly Lys Ala Ala Ser Phe
145                 150                 155                 160

aca ttt cgt aaa aca gga gaa aga aaa act gaa gtt gtt ggt ggt gca      528
Thr Phe Arg Lys Thr Gly Glu Arg Lys Thr Glu Val Val Gly Gly Ala
                165                 170                 175

gac att tac atg cca gtg tgc cga cgg cac tat gta aat ggg caa att      576
Asp Ile Tyr Met Pro Val Cys Arg Arg His Tyr Val Asn Gly Gln Ile
            180                 185                 190

gtt att gat aca acg agg gct gtg ctg gaa tcc ccg gag gtg caa tat      624
Val Ile Asp Thr Thr Arg Ala Val Leu Glu Ser Pro Glu Val Gln Tyr
        195                 200                 205
```

```
gat gct tgt gca caa gca acc aca aca tct gga taa                  660
Asp Ala Cys Ala Gln Ala Thr Thr Thr Ser Gly
    210                 215


<210> SEQ ID NO 2
<211> LENGTH: 219
<212> TYPE: PRT
<213> ORGANISM: Pinus taeda

<400> SEQUENCE: 2

Met Asp Asp Ser Gly Ile Tyr Thr Ser Gly Glu Ile His Leu Ile Leu
1               5                   10                  15

Gly Pro Met Phe Ala Gly Lys Thr Thr Ala Leu Ile Arg Lys Met Arg
            20                  25                  30

Ala Glu Ile Gln Met Gly Arg Arg Val Val Leu Val Lys Ser Asp Lys
        35                  40                  45

Asp Thr Arg Tyr Gly Leu Asn Ser Val Val Ser His Asp Gly Ala Lys
    50                  55                  60

Met Pro Cys Trp Ala Val Ala Asp Leu Ala Ser Phe Lys Gly Lys Leu
65                  70                  75                  80

Gly Glu Glu Ala Tyr Lys Gln Val Asp Val Ile Gly Ile Asp Glu Ala
                85                  90                  95

Gln Phe Phe Lys Asp Leu Tyr Ser Phe Cys Gln Val Ala Ala Asp Arg
            100                 105                 110

Asp Gly Lys Ile Val Ile Val Ala Gly Leu Asp Gly Asp Tyr Leu Arg
        115                 120                 125

Lys Ser Phe Gly Ser Ala Leu Glu Leu Ile Pro Ile Ala Asp Ser Val
    130                 135                 140

Val Lys Leu Lys Ser Arg Cys Glu Leu Cys Gly Lys Ala Ala Ser Phe
145                 150                 155                 160

Thr Phe Arg Lys Thr Gly Glu Arg Lys Thr Glu Val Val Gly Gly Ala
                165                 170                 175

Asp Ile Tyr Met Pro Val Cys Arg Arg His Tyr Val Asn Gly Gln Ile
            180                 185                 190

Val Ile Asp Thr Thr Arg Ala Val Leu Glu Ser Pro Glu Val Gln Tyr
        195                 200                 205

Asp Ala Cys Ala Gln Ala Thr Thr Thr Ser Gly
    210                 215


<210> SEQ ID NO 3
<211> LENGTH: 705
<212> TYPE: DNA
<213> ORGANISM: Lycopersicon esculentum
<220> FEATURE:
<221> NAME/KEY: CDS
<222> LOCATION: (1)..(705)

<400> SEQUENCE: 3

atg gct ttt tca tca tct gct aga aac cca gtt gac ctg aga aat gga       48
Met Ala Phe Ser Ser Ser Ala Arg Asn Pro Val Asp Leu Arg Asn Gly
1               5                   10                  15

tcg aag aac agt ttt tgt ccg gtg ggt gaa ata cat gta att gtt ggt       96
Ser Lys Asn Ser Phe Cys Pro Val Gly Glu Ile His Val Ile Val Gly
            20                  25                  30

cct atg ttt gct gga aaa acc act gct ctt ctt cgc cgg gtc aat ttg      144
Pro Met Phe Ala Gly Lys Thr Thr Ala Leu Leu Arg Arg Val Asn Leu
        35                  40                  45

gaa tcc aac gat ggg aga aat gtg gta ctg att aag tca agt aaa gat      192
Glu Ser Asn Asp Gly Arg Asn Val Val Leu Ile Lys Ser Ser Lys Asp
    50                  55                  60
```

```
gca aga tat gct gta gat gca gtg gtg aca cat gat ggg aca aga ttt      240
Ala Arg Tyr Ala Val Asp Ala Val Val Thr His Asp Gly Thr Arg Phe
65                  70                  75                  80

cca tgt tgg tca ttg ccg gat ctt tca tct ttc aag cag aga ttt gga      288
Pro Cys Trp Ser Leu Pro Asp Leu Ser Ser Phe Lys Gln Arg Phe Gly
                85                  90                  95

aaa gat gca tat gaa aag gtg gat gtg att ggc atc gat gaa gct cag      336
Lys Asp Ala Tyr Glu Lys Val Asp Val Ile Gly Ile Asp Glu Ala Gln
            100                 105                 110

ttc ttt ggg gac ctt tat gag ttc tgc tgc aat gct gct gat ttt gat      384
Phe Phe Gly Asp Leu Tyr Glu Phe Cys Cys Asn Ala Ala Asp Phe Asp
        115                 120                 125

ggg aaa att ata gtt gtt gca ggc cta gat ggt gat tac ttg agg aag      432
Gly Lys Ile Ile Val Val Ala Gly Leu Asp Gly Asp Tyr Leu Arg Lys
    130                 135                 140

agt ttt ggt tca gtg ctt gac ata att cca ctt gct gat act gtg acc      480
Ser Phe Gly Ser Val Leu Asp Ile Ile Pro Leu Ala Asp Thr Val Thr
145                 150                 155                 160

aag ttg act gct aga tgt gag ttg tgt aac aga agg gca ttt ttc acc      528
Lys Leu Thr Ala Arg Cys Glu Leu Cys Asn Arg Arg Ala Phe Phe Thr
                165                 170                 175

ttc aga aag act aat gag aca gag act gag ctt ata gga ggt gct gat      576
Phe Arg Lys Thr Asn Glu Thr Glu Thr Glu Leu Ile Gly Gly Ala Asp
            180                 185                 190

att tac atg cct gtt tgt cgt cag cac tat gtt aat gga caa tct gtc      624
Ile Tyr Met Pro Val Cys Arg Gln His Tyr Val Asn Gly Gln Ser Val
        195                 200                 205

aat gaa tct gca aaa atg gtt ctt gaa tct cat aaa gtg tca aat gaa      672
Asn Glu Ser Ala Lys Met Val Leu Glu Ser His Lys Val Ser Asn Glu
    210                 215                 220

ctt atc tta gaa tca cca cta gtt gat cca taa                          705
Leu Ile Leu Glu Ser Pro Leu Val Asp Pro
225                 230


<210> SEQ ID NO 4
<211> LENGTH: 234
<212> TYPE: PRT
<213> ORGANISM: Lycopersicon esculentum

<400> SEQUENCE: 4

Met Ala Phe Ser Ser Ser Ala Arg Asn Pro Val Asp Leu Arg Asn Gly
1               5                   10                  15

Ser Lys Asn Ser Phe Cys Pro Val Gly Glu Ile His Val Ile Val Gly
            20                  25                  30

Pro Met Phe Ala Gly Lys Thr Thr Ala Leu Leu Arg Arg Val Asn Leu
        35                  40                  45

Glu Ser Asn Asp Gly Arg Asn Val Val Leu Ile Lys Ser Ser Lys Asp
    50                  55                  60

Ala Arg Tyr Ala Val Asp Ala Val Val Thr His Asp Gly Thr Arg Phe
65                  70                  75                  80

Pro Cys Trp Ser Leu Pro Asp Leu Ser Ser Phe Lys Gln Arg Phe Gly
                85                  90                  95

Lys Asp Ala Tyr Glu Lys Val Asp Val Ile Gly Ile Asp Glu Ala Gln
            100                 105                 110

Phe Phe Gly Asp Leu Tyr Glu Phe Cys Cys Asn Ala Ala Asp Phe Asp
        115                 120                 125

Gly Lys Ile Ile Val Val Ala Gly Leu Asp Gly Asp Tyr Leu Arg Lys
    130                 135                 140
```

```
Ser Phe Gly Ser Val Leu Asp Ile Ile Pro Leu Ala Asp Thr Val Thr
145                 150                 155                 160

Lys Leu Thr Ala Arg Cys Glu Leu Cys Asn Arg Arg Ala Phe Phe Thr
                165                 170                 175

Phe Arg Lys Thr Asn Glu Thr Glu Thr Glu Leu Ile Gly Gly Ala Asp
            180                 185                 190

Ile Tyr Met Pro Val Cys Arg Gln His Tyr Val Asn Gly Gln Ser Val
        195                 200                 205

Asn Glu Ser Ala Lys Met Val Leu Glu Ser His Lys Val Ser Asn Glu
    210                 215                 220

Leu Ile Leu Glu Ser Pro Leu Val Asp Pro
225                 230


<210> SEQ ID NO 5
<211> LENGTH: 208
<212> TYPE: PRT
<213> ORGANISM: Lycopersicon esculentum

<400> SEQUENCE: 5

Met Ala Phe Ser Ser Ser Ala Arg Asn Pro Val Asp Leu Arg Asn Gly
1               5                   10                  15

Ser Lys Asn Ser Phe Cys Pro Val Gly Glu Ile His Val Ile Val Gly
            20                  25                  30

Pro Met Phe Ala Gly Lys Thr Thr Ala Leu Leu Arg Arg Val Asn Leu
        35                  40                  45

Glu Ser Asn Asp Gly Arg Asn Val Val Leu Ile Lys Ser Ser Lys Asp
    50                  55                  60

Ala Arg Tyr Ala Val Asp Ala Val Val Thr His Asp Gly Thr Arg Phe
65                  70                  75                  80

Pro Cys Trp Ser Leu Pro Asp Leu Ser Ser Phe Lys Gln Arg Phe Gly
                85                  90                  95

Lys Asp Ala Tyr Glu Lys Val Asp Val Ile Gly Ile Asp Glu Ala Gln
            100                 105                 110

Phe Phe Gly Asp Leu Tyr Glu Phe Cys Cys Asn Ala Ala Asp Phe Asp
        115                 120                 125

Gly Lys Ile Ile Val Val Ala Gly Leu Asp Gly Asp Tyr Leu Arg Lys
    130                 135                 140

Ser Phe Gly Ser Val Leu Asp Ile Ile Pro Leu Ala Asp Thr Val Thr
145                 150                 155                 160

Lys Leu Thr Ala Arg Cys Glu Leu Cys Asn Arg Arg Ala Phe Phe Thr
                165                 170                 175

Phe Arg Lys Thr Asn Glu Thr Glu Thr Glu Leu Ile Gly Gly Ala Asp
            180                 185                 190

Ile Tyr Met Pro Val Cys Arg Gln His Tyr Val Asn Gly Gln Ser Val
        195                 200                 205


<210> SEQ ID NO 6
<211> LENGTH: 831
<212> TYPE: DNA
<213> ORGANISM: Oryza sativa
<220> FEATURE:
<221> NAME/KEY: CDS
<222> LOCATION: (1)..(831)

<400> SEQUENCE: 6

atg agc tcc att tgc gcc atg aga tcc ctc ctc gcc gcc tcc acc ttc       48
Met Ser Ser Ile Cys Ala Met Arg Ser Leu Leu Ala Ala Ser Thr Phe
1               5                   10                  15
```

```
ctc cgc tcc ggc gct tcc cct ctg ctg cgg ccc ctt tcc cgt cct ctc       96
Leu Arg Ser Gly Ala Ser Pro Leu Leu Arg Pro Leu Ser Arg Pro Leu
            20                  25                  30

cct tcc cgc ctg aat ctt tcc cga ttc ggt ccg gtg agg ccg gtc tct      144
Pro Ser Arg Leu Asn Leu Ser Arg Phe Gly Pro Val Arg Pro Val Ser
        35                  40                  45

gcg gcg gcg gcg gcg gcg gac aag tct cga ggc gga ggc ggc tcc gcg      192
Ala Ala Ala Ala Ala Ala Asp Lys Ser Arg Gly Gly Gly Gly Ser Ala
    50                  55                  60

atg gag gcc cag ccg tcg tat ccc ggt gag att cac gtc atc gtg ggc      240
Met Glu Ala Gln Pro Ser Tyr Pro Gly Glu Ile His Val Ile Val Gly
65                  70                  75                  80

ccc atg ttc gcc ggg aag acc act gcc ctt ctc cga cgc gtg cag gtc      288
Pro Met Phe Ala Gly Lys Thr Thr Ala Leu Leu Arg Arg Val Gln Val
                85                  90                  95

gag gcc ggc act ggc agg aac gtg gca ctc atc aag tct gac aag gac      336
Glu Ala Gly Thr Gly Arg Asn Val Ala Leu Ile Lys Ser Asp Lys Asp
            100                 105                 110

aat agg tat gga ttg gat tct gtc gta act cat gat ggc aca aag atg      384
Asn Arg Tyr Gly Leu Asp Ser Val Val Thr His Asp Gly Thr Lys Met
        115                 120                 125

cca tgc tgg gct cta cct gag ctt tca agt ttc caa gat aaa tta gga      432
Pro Cys Trp Ala Leu Pro Glu Leu Ser Ser Phe Gln Asp Lys Leu Gly
    130                 135                 140

aca gag gct tac gat aag gtt gat gtc ata ggt att gat gaa gca cag      480
Thr Glu Ala Tyr Asp Lys Val Asp Val Ile Gly Ile Asp Glu Ala Gln
145                 150                 155                 160

ttt ttt gac gat ctt cat gat ttc tgc tgc aaa gct gct gac cgt gat      528
Phe Phe Asp Asp Leu His Asp Phe Cys Cys Lys Ala Ala Asp Arg Asp
                165                 170                 175

gga aaa att gtt gta gtc gca ggg cta gat ggt gac tac aaa agg aac      576
Gly Lys Ile Val Val Val Ala Gly Leu Asp Gly Asp Tyr Lys Arg Asn
            180                 185                 190

aaa ttt ggg tca gtt ctg gac att ata ccc ttg gct gac tcg gtc acc      624
Lys Phe Gly Ser Val Leu Asp Ile Ile Pro Leu Ala Asp Ser Val Thr
        195                 200                 205

aag ctc acc gca cgc tgt gag ttg tgc ggt cgc cgt gca ttc ttc acg      672
Lys Leu Thr Ala Arg Cys Glu Leu Cys Gly Arg Arg Ala Phe Phe Thr
    210                 215                 220

ctg agg aag aca cgg gaa act aag acc gag ctc att gga gga gct gat      720
Leu Arg Lys Thr Arg Glu Thr Lys Thr Glu Leu Ile Gly Gly Ala Asp
225                 230                 235                 240

gtg tac atg cct gta tgt agg caa cac tac ctg gat ggt cag att gtc      768
Val Tyr Met Pro Val Cys Arg Gln His Tyr Leu Asp Gly Gln Ile Val
                245                 250                 255

att gag gcc aca agg att gtg ctg gat ctt gaa aaa tcc aag gtt atc      816
Ile Glu Ala Thr Arg Ile Val Leu Asp Leu Glu Lys Ser Lys Val Ile
            260                 265                 270

cat gct ttc aag tga                                                  831
His Ala Phe Lys
        275


<210> SEQ ID NO 7
<211> LENGTH: 276
<212> TYPE: PRT
<213> ORGANISM: Oryza sativa

<400> SEQUENCE: 7

Met Ser Ser Ile Cys Ala Met Arg Ser Leu Leu Ala Ala Ser Thr Phe
1               5                   10                  15

Leu Arg Ser Gly Ala Ser Pro Leu Leu Arg Pro Leu Ser Arg Pro Leu
```

```
            20                  25                  30

Pro Ser Arg Leu Asn Leu Ser Arg Phe Gly Pro Val Arg Pro Val Ser
        35                  40                  45

Ala Ala Ala Ala Ala Ala Asp Lys Ser Arg Gly Gly Gly Gly Ser Ala
    50                  55                  60

Met Glu Ala Gln Pro Ser Tyr Pro Gly Glu Ile His Val Ile Val Gly
65                  70                  75                  80

Pro Met Phe Ala Gly Lys Thr Thr Ala Leu Leu Arg Arg Val Gln Val
                85                  90                  95

Glu Ala Gly Thr Gly Arg Asn Val Ala Leu Ile Lys Ser Asp Lys Asp
            100                 105                 110

Asn Arg Tyr Gly Leu Asp Ser Val Val Thr His Asp Gly Thr Lys Met
        115                 120                 125

Pro Cys Trp Ala Leu Pro Glu Leu Ser Ser Phe Gln Asp Lys Leu Gly
    130                 135                 140

Thr Glu Ala Tyr Asp Lys Val Asp Val Ile Gly Ile Asp Glu Ala Gln
145                 150                 155                 160

Phe Phe Asp Asp Leu His Asp Phe Cys Cys Lys Ala Ala Asp Arg Asp
                165                 170                 175

Gly Lys Ile Val Val Val Ala Gly Leu Asp Gly Asp Tyr Lys Arg Asn
            180                 185                 190

Lys Phe Gly Ser Val Leu Asp Ile Ile Pro Leu Ala Asp Ser Val Thr
        195                 200                 205

Lys Leu Thr Ala Arg Cys Glu Leu Cys Gly Arg Arg Ala Phe Phe Thr
    210                 215                 220

Leu Arg Lys Thr Arg Glu Thr Lys Thr Glu Leu Ile Gly Gly Ala Asp
225                 230                 235                 240

Val Tyr Met Pro Val Cys Arg Gln His Tyr Leu Asp Gly Gln Ile Val
                245                 250                 255

Ile Glu Ala Thr Arg Ile Val Leu Asp Leu Glu Lys Ser Lys Val Ile
            260                 265                 270

His Ala Phe Lys
        275


<210> SEQ ID NO 8
<211> LENGTH: 717
<212> TYPE: DNA
<213> ORGANISM: Arabidopsis thaliana
<220> FEATURE:
<221> NAME/KEY: CDS
<222> LOCATION: (1)..(717)

<400> SEQUENCE: 8

atg gcg act ctc aaa gct tcc ttt ttg atc aaa acc ctc gac agt gac       48
Met Ala Thr Leu Lys Ala Ser Phe Leu Ile Lys Thr Leu Asp Ser Asp
1               5                   10                  15

gtc acc gga gat ttt ctc tcc gat ctg gaa cgt cgt ggg tca ggt gct       96
Val Thr Gly Asp Phe Leu Ser Asp Leu Glu Arg Arg Gly Ser Gly Ala
            20                  25                  30

gtt cat gtt atc atg ggt cct atg ttt tct ggg aaa tcg acc tct ctc      144
Val His Val Ile Met Gly Pro Met Phe Ser Gly Lys Ser Thr Ser Leu
        35                  40                  45

ctt cgc cga atc aag tca gag atc agc gac gga aga agt gtt gcg atg      192
Leu Arg Arg Ile Lys Ser Glu Ile Ser Asp Gly Arg Ser Val Ala Met
    50                  55                  60

ctg aaa tcg agt aag gat acg aga tac gca aaa gat tcg gtg gtg aca      240
Leu Lys Ser Ser Lys Asp Thr Arg Tyr Ala Lys Asp Ser Val Val Thr
65                  70                  75                  80
```

```
cat gat gga att gga ttc cct tgc tgg gct ctt cca gat ctc atg tca      288
His Asp Gly Ile Gly Phe Pro Cys Trp Ala Leu Pro Asp Leu Met Ser
                85                  90                  95

ttt cct gag aaa ttc gga cta gat gct tat aac aag ctt gat gtg att      336
Phe Pro Glu Lys Phe Gly Leu Asp Ala Tyr Asn Lys Leu Asp Val Ile
            100                 105                 110

ggt att gat gag gct cag ttc ttt gga gat ctt tat gag ttt tgc tgc      384
Gly Ile Asp Glu Ala Gln Phe Phe Gly Asp Leu Tyr Glu Phe Cys Cys
        115                 120                 125

aaa gtc gct gat gat gat ggt aaa att gtg atc gtt gct ggc cta gat      432
Lys Val Ala Asp Asp Asp Gly Lys Ile Val Ile Val Ala Gly Leu Asp
    130                 135                 140

ggt gac tat tta agg agg agt ttt ggg gct gta ctt gac att ata cca      480
Gly Asp Tyr Leu Arg Arg Ser Phe Gly Ala Val Leu Asp Ile Ile Pro
145                 150                 155                 160

ata gct gat tct gtg act aag cta act gca agg tgt gag gtc tgt gga      528
Ile Ala Asp Ser Val Thr Lys Leu Thr Ala Arg Cys Glu Val Cys Gly
                165                 170                 175

cat aaa gct ttc ttc act tta aga aag aat tgt gac acc aga act gag      576
His Lys Ala Phe Phe Thr Leu Arg Lys Asn Cys Asp Thr Arg Thr Glu
            180                 185                 190

ctt att ggt gga gct gat gtc tat atg cct gtt tgt cgc aag cat tac      624
Leu Ile Gly Gly Ala Asp Val Tyr Met Pro Val Cys Arg Lys His Tyr
        195                 200                 205

atc act aat cat att gtt att aaa gcc tct aag aaa gtc ttg gaa gat      672
Ile Thr Asn His Ile Val Ile Lys Ala Ser Lys Lys Val Leu Glu Asp
    210                 215                 220

tct gac aag gct aga gct gaa tcc tgt gtt gct gct aca atc taa          717
Ser Asp Lys Ala Arg Ala Glu Ser Cys Val Ala Ala Thr Ile
225                 230                 235


<210> SEQ ID NO 9
<211> LENGTH: 238
<212> TYPE: PRT
<213> ORGANISM: Arabidopsis thaliana

<400> SEQUENCE: 9

Met Ala Thr Leu Lys Ala Ser Phe Leu Ile Lys Thr Leu Asp Ser Asp
1               5                   10                  15

Val Thr Gly Asp Phe Leu Ser Asp Leu Glu Arg Arg Gly Ser Gly Ala
            20                  25                  30

Val His Val Ile Met Gly Pro Met Phe Ser Gly Lys Ser Thr Ser Leu
        35                  40                  45

Leu Arg Arg Ile Lys Ser Glu Ile Ser Asp Gly Arg Ser Val Ala Met
    50                  55                  60

Leu Lys Ser Ser Lys Asp Thr Arg Tyr Ala Lys Asp Ser Val Val Thr
65                  70                  75                  80

His Asp Gly Ile Gly Phe Pro Cys Trp Ala Leu Pro Asp Leu Met Ser
                85                  90                  95

Phe Pro Glu Lys Phe Gly Leu Asp Ala Tyr Asn Lys Leu Asp Val Ile
            100                 105                 110

Gly Ile Asp Glu Ala Gln Phe Phe Gly Asp Leu Tyr Glu Phe Cys Cys
        115                 120                 125

Lys Val Ala Asp Asp Asp Gly Lys Ile Val Ile Val Ala Gly Leu Asp
    130                 135                 140

Gly Asp Tyr Leu Arg Arg Ser Phe Gly Ala Val Leu Asp Ile Ile Pro
145                 150                 155                 160

Ile Ala Asp Ser Val Thr Lys Leu Thr Ala Arg Cys Glu Val Cys Gly
```

```
                165                 170                 175

His Lys Ala Phe Phe Thr Leu Arg Lys Asn Cys Asp Thr Arg Thr Glu
            180                 185                 190

Leu Ile Gly Gly Ala Asp Val Tyr Met Pro Val Cys Arg Lys His Tyr
        195                 200                 205

Ile Thr Asn His Ile Val Ile Lys Ala Ser Lys Lys Val Leu Glu Asp
    210                 215                 220

Ser Asp Lys Ala Arg Ala Glu Ser Cys Val Ala Ala Thr Ile
225                 230                 235


<210> SEQ ID NO 10
<211> LENGTH: 645
<212> TYPE: DNA
<213> ORGANISM: Arabidopsis thaliana
<220> FEATURE:
<221> NAME/KEY: CDS
<222> LOCATION: (1)..(645)

<400> SEQUENCE: 10

atg gcg act ctc aaa gct tcc ttt ttg atc aaa acc ctc gac agt gac       48
Met Ala Thr Leu Lys Ala Ser Phe Leu Ile Lys Thr Leu Asp Ser Asp
1               5                   10                  15

gtc acc gga gat ttt ctc tcc gat ctg gaa cgt cgt ggg tca ggt gct       96
Val Thr Gly Asp Phe Leu Ser Asp Leu Glu Arg Arg Gly Ser Gly Ala
            20                  25                  30

gtt cat gtt atc atg ggt cct atg ttt tct ggg aaa tcg acc tct ctc      144
Val His Val Ile Met Gly Pro Met Phe Ser Gly Lys Ser Thr Ser Leu
        35                  40                  45

ctt cgc cga atc aag tca gag atc agc gac gga aga agt gtt gcg atg      192
Leu Arg Arg Ile Lys Ser Glu Ile Ser Asp Gly Arg Ser Val Ala Met
    50                  55                  60

ctg aaa tcg agt aag gat acg aga tac gca aaa gat tcg gtg gtg aca      240
Leu Lys Ser Ser Lys Asp Thr Arg Tyr Ala Lys Asp Ser Val Val Thr
65                  70                  75                  80

cat gat gga att gga ttc cct tgc tgg gct ctt cca gat ctc atg tca      288
His Asp Gly Ile Gly Phe Pro Cys Trp Ala Leu Pro Asp Leu Met Ser
                85                  90                  95

ttt cct gag aaa ttc gga cta gat gct tat aac aag ctt gat gtg att      336
Phe Pro Glu Lys Phe Gly Leu Asp Ala Tyr Asn Lys Leu Asp Val Ile
            100                 105                 110

ggt att gat gag gct cag ttc ttt gga gat ctt tat gag ttt tgc tgc      384
Gly Ile Asp Glu Ala Gln Phe Phe Gly Asp Leu Tyr Glu Phe Cys Cys
        115                 120                 125

aaa gtc gct gat gat gat ggt aaa att gtg atc gtt gct ggc cta gat      432
Lys Val Ala Asp Asp Asp Gly Lys Ile Val Ile Val Ala Gly Leu Asp
    130                 135                 140

ggt gac tat tta agg agg agt ttt ggg gct gta ctt gac att ata cca      480
Gly Asp Tyr Leu Arg Arg Ser Phe Gly Ala Val Leu Asp Ile Ile Pro
145                 150                 155                 160

ata gct gat tct gtg act aag cta act gca agg tgt gag gtc tgt gga      528
Ile Ala Asp Ser Val Thr Lys Leu Thr Ala Arg Cys Glu Val Cys Gly
                165                 170                 175

cat aaa gct ttc ttc act tta aga aag aat tgt gac acc aga act gag      576
His Lys Ala Phe Phe Thr Leu Arg Lys Asn Cys Asp Thr Arg Thr Glu
            180                 185                 190

ctt att ggt gga gct gat gtc tat atg cct gtt tgt cgc aag cat tac      624
Leu Ile Gly Gly Ala Asp Val Tyr Met Pro Val Cys Arg Lys His Tyr
        195                 200                 205

atc act aat cat att gtt taa                                          645
Ile Thr Asn His Ile Val
    210
```

<210> SEQ ID NO 11
<211> LENGTH: 214
<212> TYPE: PRT
<213> ORGANISM: Arabidopsis thaliana

<400> SEQUENCE: 11

```
Met Ala Thr Leu Lys Ala Ser Phe Leu Ile Lys Thr Leu Asp Ser Asp
1               5                   10                  15

Val Thr Gly Asp Phe Leu Ser Asp Leu Glu Arg Arg Gly Ser Gly Ala
            20                  25                  30

Val His Val Ile Met Gly Pro Met Phe Ser Gly Lys Ser Thr Ser Leu
        35                  40                  45

Leu Arg Arg Ile Lys Ser Glu Ile Ser Asp Gly Arg Ser Val Ala Met
    50                  55                  60

Leu Lys Ser Ser Lys Asp Thr Arg Tyr Ala Lys Asp Ser Val Val Thr
65                  70                  75                  80

His Asp Gly Ile Gly Phe Pro Cys Trp Ala Leu Pro Asp Leu Met Ser
                85                  90                  95

Phe Pro Glu Lys Phe Gly Leu Asp Ala Tyr Asn Lys Leu Asp Val Ile
            100                 105                 110

Gly Ile Asp Glu Ala Gln Phe Phe Gly Asp Leu Tyr Glu Phe Cys Cys
        115                 120                 125

Lys Val Ala Asp Asp Asp Gly Lys Ile Val Ile Val Ala Gly Leu Asp
    130                 135                 140

Gly Asp Tyr Leu Arg Arg Ser Phe Gly Ala Val Leu Asp Ile Ile Pro
145                 150                 155                 160

Ile Ala Asp Ser Val Thr Lys Leu Thr Ala Arg Cys Glu Val Cys Gly
                165                 170                 175

His Lys Ala Phe Phe Thr Leu Arg Lys Asn Cys Asp Thr Arg Thr Glu
            180                 185                 190

Leu Ile Gly Gly Ala Asp Val Tyr Met Pro Val Cys Arg Lys His Tyr
        195                 200                 205

Ile Thr Asn His Ile Val
    210
```

<210> SEQ ID NO 12
<211> LENGTH: 834
<212> TYPE: DNA
<213> ORGANISM: Arabidopsis thaliana
<220> FEATURE:
<221> NAME/KEY: CDS
<222> LOCATION: (1)..(834)

<400> SEQUENCE: 12

```
atg aga aca tta atc tca cca tct ctt gct ccc ttc tct ctt cat ctc       48
Met Arg Thr Leu Ile Ser Pro Ser Leu Ala Pro Phe Ser Leu His Leu
1               5                   10                  15

cat aaa ccc tct ctc ttc tcc acc gct ctt cgc ttc tcc ttc tca atc       96
His Lys Pro Ser Leu Phe Ser Thr Ala Leu Arg Phe Ser Phe Ser Ile
            20                  25                  30

aac aac ata acc ccc aca aat tca cct cct tcc acc att tcc acc aga      144
Asn Asn Ile Thr Pro Thr Asn Ser Pro Pro Ser Thr Ile Ser Thr Arg
        35                  40                  45

aag cta caa acg aaa gcg acg agg gta aca tca tca tca tca tct cag      192
Lys Leu Gln Thr Lys Ala Thr Arg Val Thr Ser Ser Ser Ser Ser Gln
    50                  55                  60

ccg ctc tcc tcc tca tct ccc ggc gaa atc cac gtc gta gtc ggt cca      240
Pro Leu Ser Ser Ser Ser Pro Gly Glu Ile His Val Val Val Gly Pro
```

```
65                  70                  75                  80

atg ttc tcc ggt aaa aca aca aca ctt ctc cgc cgt ata ctc gcc gaa      288
Met Phe Ser Gly Lys Thr Thr Thr Leu Leu Arg Arg Ile Leu Ala Glu
                85                  90                  95

aga gaa acc ggt aaa aga atc gca atc atc aaa tcc aac aaa gac aca      336
Arg Glu Thr Gly Lys Arg Ile Ala Ile Ile Lys Ser Asn Lys Asp Thr
            100                 105                 110

aga tac tgc acc gaa tca ata gtt act cac gac ggt gag aaa tac cct      384
Arg Tyr Cys Thr Glu Ser Ile Val Thr His Asp Gly Glu Lys Tyr Pro
        115                 120                 125

tgc tgg tca ctc ccc gat ctc tcg tcc ttc aaa gag aga ttc gga ttc      432
Cys Trp Ser Leu Pro Asp Leu Ser Ser Phe Lys Glu Arg Phe Gly Phe
    130                 135                 140

gac gac tac gag aat cga tta gat gtg att gga atc gac gaa gct caa      480
Asp Asp Tyr Glu Asn Arg Leu Asp Val Ile Gly Ile Asp Glu Ala Gln
145                 150                 155                 160

ttc ttc gga gat ctt tac gag ttt tgc cgt gaa gct gct gat aaa gag      528
Phe Phe Gly Asp Leu Tyr Glu Phe Cys Arg Glu Ala Ala Asp Lys Glu
                165                 170                 175

ggt aaa act gta att gtt gct gga ttg gat ggt gat ttt atg agg agg      576
Gly Lys Thr Val Ile Val Ala Gly Leu Asp Gly Asp Phe Met Arg Arg
            180                 185                 190

agg ttt ggt tcg gtt ctt gat ttg att ccg att gcg gat acg gtt acg      624
Arg Phe Gly Ser Val Leu Asp Leu Ile Pro Ile Ala Asp Thr Val Thr
        195                 200                 205

aag ctg acg tca cgg tgt gag gtt tgt ggg aag aga gct ttg ttt acg      672
Lys Leu Thr Ser Arg Cys Glu Val Cys Gly Lys Arg Ala Leu Phe Thr
    210                 215                 220

atg agg aag acg gag gag aaa gag acg gag ttg atc ggt ggt gct gaa      720
Met Arg Lys Thr Glu Glu Lys Glu Thr Glu Leu Ile Gly Gly Ala Glu
225                 230                 235                 240

gtt tat atg cct gtg tgt agg agt cat tac gtt tgc ggt caa aac gtt      768
Val Tyr Met Pro Val Cys Arg Ser His Tyr Val Cys Gly Gln Asn Val
                245                 250                 255

ttg gaa acc gct cgt gcc gtt ttg gat tca agc aat aat cat agt gtt      816
Leu Glu Thr Ala Arg Ala Val Leu Asp Ser Ser Asn Asn His Ser Val
            260                 265                 270

gta gca agt tca ctt tag                                              834
Val Ala Ser Ser Leu
        275


<210> SEQ ID NO 13
<211> LENGTH: 277
<212> TYPE: PRT
<213> ORGANISM: Arabidopsis thaliana

<400> SEQUENCE: 13

Met Arg Thr Leu Ile Ser Pro Ser Leu Ala Pro Phe Ser Leu His Leu
1               5                   10                  15

His Lys Pro Ser Leu Phe Ser Thr Ala Leu Arg Phe Ser Phe Ser Ile
            20                  25                  30

Asn Asn Ile Thr Pro Thr Asn Ser Pro Pro Ser Thr Ile Ser Thr Arg
        35                  40                  45

Lys Leu Gln Thr Lys Ala Thr Arg Val Thr Ser Ser Ser Ser Ser Gln
    50                  55                  60

Pro Leu Ser Ser Ser Ser Pro Gly Glu Ile His Val Val Val Gly Pro
65                  70                  75                  80

Met Phe Ser Gly Lys Thr Thr Thr Leu Leu Arg Arg Ile Leu Ala Glu
                85                  90                  95
```

Arg Glu Thr Gly Lys Arg Ile Ala Ile Ile Lys Ser Asn Lys Asp Thr
100 105 110

Arg Tyr Cys Thr Glu Ser Ile Val Thr His Asp Gly Glu Lys Tyr Pro
115 120 125

Cys Trp Ser Leu Pro Asp Leu Ser Ser Phe Lys Glu Arg Phe Gly Phe
130 135 140

Asp Asp Tyr Glu Asn Arg Leu Asp Val Ile Gly Ile Asp Glu Ala Gln
145 150 155 160

Phe Phe Gly Asp Leu Tyr Glu Phe Cys Arg Glu Ala Ala Asp Lys Glu
165 170 175

Gly Lys Thr Val Ile Val Ala Gly Leu Asp Gly Asp Phe Met Arg Arg
180 185 190

Arg Phe Gly Ser Val Leu Asp Leu Ile Pro Ile Ala Asp Thr Val Thr
195 200 205

Lys Leu Thr Ser Arg Cys Glu Val Cys Gly Lys Arg Ala Leu Phe Thr
210 215 220

Met Arg Lys Thr Glu Glu Lys Glu Thr Glu Leu Ile Gly Gly Ala Glu
225 230 235 240

Val Tyr Met Pro Val Cys Arg Ser His Tyr Val Cys Gly Gln Asn Val
245 250 255

Leu Glu Thr Ala Arg Ala Val Leu Asp Ser Ser Asn Asn His Ser Val
260 265 270

Val Ala Ser Ser Leu
275

<210> SEQ ID NO 14
<211> LENGTH: 36
<212> TYPE: DNA
<213> ORGANISM: Artificial sequence
<220> FEATURE:
<223> OTHER INFORMATION: PCR primer

<400> SEQUENCE: 14
ccgctcgaga tggcgactct caaagcttcc tttttg 36

<210> SEQ ID NO 15
<211> LENGTH: 36
<212> TYPE: DNA
<213> ORGANISM: Artificial sequence
<220> FEATURE:
<223> OTHER INFORMATION: PCR-primer

<400> SEQUENCE: 15
cgcggatcct tagattgtag cagcaacaca ggattc 36

<210> SEQ ID NO 16
<211> LENGTH: 40
<212> TYPE: DNA
<213> ORGANISM: Artificial sequence
<220> FEATURE:
<223> OTHER INFORMATION: PCR-primer

<400> SEQUENCE: 16
cgcggatcct taaacaatat gattagtgat gtaatgcttg 40

<210> SEQ ID NO 17
<211> LENGTH: 39
<212> TYPE: DNA
<213> ORGANISM: Artificial sequence
<220> FEATURE:
<223> OTHER INFORMATION: PRC-primer

<400> SEQUENCE: 17
ggaagatctt tagacagatt gtccattaac atagtgctg 39

<210> SEQ ID NO 18
<211> LENGTH: 37
<212> TYPE: DNA
<213> ORGANISM: Artificial sequence
<220> FEATURE:
<223> OTHER INFORMATION: PCR-primer

<400> SEQUENCE: 18
ggaagatctt tatggatcaa ctagtggtga ttctaag 37

<210> SEQ ID NO 19
<211> LENGTH: 36
<212> TYPE: DNA
<213> ORGANISM: Artificial sequence
<220> FEATURE:
<223> OTHER INFORMATION: PCR-primer

<400> SEQUENCE: 19
ccgctcgaga tggctttttc atcatctgct agaaac 36

<210> SEQ ID NO 20
<211> LENGTH: 34
<212> TYPE: DNA
<213> ORGANISM: Artificial sequence
<220> FEATURE:
<223> OTHER INFORMATION: PCR-primer

<400> SEQUENCE: 20
tataggatcc gccaccatgg cttcgtaccc cggc 34

<210> SEQ ID NO 21
<211> LENGTH: 29
<212> TYPE: DNA
<213> ORGANISM: Artificial sequence
<220> FEATURE:
<223> OTHER INFORMATION: PCR-primer

<400> SEQUENCE: 21
tatactcgag gaggtcgact cagttagcc 29

<210> SEQ ID NO 22
<211> LENGTH: 50
<212> TYPE: DNA
<213> ORGANISM: Artificial sequence
<220> FEATURE:
<223> OTHER INFORMATION: PCR-primer

<400> SEQUENCE: 22
cgcggatcca tggctttttc atcatctgct agaaacccag ttgacctgag 50

<210> SEQ ID NO 23
<211> LENGTH: 37
<212> TYPE: DNA
<213> ORGANISM: Artificial sequence
<220> FEATURE:
<223> OTHER INFORMATION: PCR-primer

<400> SEQUENCE: 23
ccggaattct tatggatcaa ctagtggtga ttctaag 37

<210> SEQ ID NO 24
<211> LENGTH: 46
<212> TYPE: DNA

```
<213> ORGANISM: Artificial sequence
<220> FEATURE:
<223> OTHER INFORMATION: PCR-primer

<400> SEQUENCE: 24

cgcggatcca tggcgactct caaagcttcc tttttgatca aaaccc                46


<210> SEQ ID NO 25
<211> LENGTH: 39
<212> TYPE: DNA
<213> ORGANISM: Artificial sequence
<220> FEATURE:
<223> OTHER INFORMATION: PCR-primer

<400> SEQUENCE: 25

ccggaattct tagattgtag cagcaacaca ggattcagc                        39


<210> SEQ ID NO 26
<211> LENGTH: 25
<212> TYPE: DNA
<213> ORGANISM: Artificial sequence
<220> FEATURE:
<223> OTHER INFORMATION: PCR-primer

<400> SEQUENCE: 26

atgagaacat taatctcacc atctc                                       25


<210> SEQ ID NO 27
<211> LENGTH: 27
<212> TYPE: DNA
<213> ORGANISM: Artificial sequence
<220> FEATURE:
<223> OTHER INFORMATION: PCR-primer

<400> SEQUENCE: 27

ctaaagtgaa cttgctacaa cactatg                                     27


<210> SEQ ID NO 28
<211> LENGTH: 34
<212> TYPE: DNA
<213> ORGANISM: Artificial sequence
<220> FEATURE:
<223> OTHER INFORMATION: PCR-primer

<400> SEQUENCE: 28

cgcggatcca tgagaacatt aatctcacca tctc                             34


<210> SEQ ID NO 29
<211> LENGTH: 32
<212> TYPE: DNA
<213> ORGANISM: Artificial sequence
<220> FEATURE:
<223> OTHER INFORMATION: PCR-primer

<400> SEQUENCE: 29

ccggaattcc taaagtgaac ttgctacaac ac                               32


<210> SEQ ID NO 30
<211> LENGTH: 30
<212> TYPE: DNA
<213> ORGANISM: Artificial sequence
<220> FEATURE:
<223> OTHER INFORMATION: PCR-primer

<400> SEQUENCE: 30

cgcggatcct ccaccgctct tcgcttctcc                                  30
```

<210> SEQ ID NO 31
<211> LENGTH: 30
<212> TYPE: DNA
<213> ORGANISM: Artificial sequence
<220> FEATURE:
<223> OTHER INFORMATION: PCR-primer

<400> SEQUENCE: 31
cgcggatcct ccaccagaaa gctacaaacg 30

<210> SEQ ID NO 32
<211> LENGTH: 29
<212> TYPE: DNA
<213> ORGANISM: Artificial sequence
<220> FEATURE:
<223> OTHER INFORMATION: PCR-primer

<400> SEQUENCE: 32
cgcggatccc agccgctctc ctcctcatc 29

<210> SEQ ID NO 33
<211> LENGTH: 32
<212> TYPE: DNA
<213> ORGANISM: Artificial sequence
<220> FEATURE:
<223> OTHER INFORMATION: PCR-primer

<400> SEQUENCE: 33
cgggatccgg cggcggcggc ggacaagtct cg 32

<210> SEQ ID NO 34
<211> LENGTH: 34
<212> TYPE: DNA
<213> ORGANISM: Artificial sequence
<220> FEATURE:
<223> OTHER INFORMATION: PCR-primer

<400> SEQUENCE: 34
cggaattctt acttgaaagc atggataacc ttgg 34

<210> SEQ ID NO 35
<211> LENGTH: 31
<212> TYPE: DNA
<213> ORGANISM: Artificial sequence
<220> FEATURE:
<223> OTHER INFORMATION: PCR-primer

<400> SEQUENCE: 35
cgcggatcca tggcttcgta ccccggccat c 31

<210> SEQ ID NO 36
<211> LENGTH: 33
<212> TYPE: DNA
<213> ORGANISM: Artificial sequence
<220> FEATURE:
<223> OTHER INFORMATION: PCR-primer

<400> SEQUENCE: 36
ccggaattct tagttagcct cccccatctc ccg 33

<210> SEQ ID NO 37
<211> LENGTH: 10
<212> TYPE: PRT
<213> ORGANISM: Artificial
<220> FEATURE:
<223> OTHER INFORMATION: Synthetic - Lid region
<220> FEATURE:

```
<221> NAME/KEY: misc_feature
<222> LOCATION: (2)..(2)
<223> OTHER INFORMATION: Xaa = Thr or Val.
<220> FEATURE:
<221> NAME/KEY: misc_feature
<222> LOCATION: (5)..(5)
<223> OTHER INFORMATION: Xaa = Thr or Lys.
<220> FEATURE:
<221> NAME/KEY: misc_feature
<222> LOCATION: (6)..(6)
<223> OTHER INFORMATION: Xaa = Ala or Ser.
<220> FEATURE:
<221> NAME/KEY: misc_feature
<222> LOCATION: (10)..(10)
<223> OTHER INFORMATION: Xaa = Leu or Val.

<400> SEQUENCE: 37

Val Xaa Lys Leu Xaa Xaa Arg Cys Glu Xaa
1               5                   10
```